(12) United States Patent
Harrison et al.

(10) Patent No.: US 11,707,564 B2
(45) Date of Patent: Jul. 25, 2023

(54) SAFE OPERATION OF INTEGRATED NEGATIVE PRESSURE WOUND TREATMENT APPARATUSES

(71) Applicant: Smith & Nephew PLC, Watford (GB)

(72) Inventors: Frederick Jethro Harrison, Cambridge (GB); Edward Yerbury Hartwell, Hull (GB); William Kelbie, Inverness (GB); Reece Knight, Kingston upon Hull (GB); Gergely Melis, Melbourn (GB); Damyn Musgrave, Cottenham (GB); Molly Northcote, Leeds (GB); Felix Clarence Quintanar, Hull (GB); Joseph William Robinson, Papworth Everard (GB); Daniel Lee Steward, Kingston upon Hull (GB); Grant West, Luton (GB)

(73) Assignee: Smith & Nephew PLC, Watford (GB)

( * ) Notice: Subject to any disclaimer, the term of this patent is extended or adjusted under 35 U.S.C. 154(b) by 514 days.

(21) Appl. No.: 16/760,314

(22) PCT Filed: Oct. 30, 2018

(86) PCT No.: PCT/EP2018/079745
§ 371 (c)(1),
(2) Date: Apr. 29, 2020

(87) PCT Pub. No.: WO2019/086475
PCT Pub. Date: May 9, 2019

(65) Prior Publication Data
US 2020/0338243 A1    Oct. 29, 2020

(30) Foreign Application Priority Data

Nov. 1, 2017 (GB) .................................. 1718054

(51) Int. Cl.
*A61M 1/00* (2006.01)
*A61F 13/00* (2006.01)
(Continued)

(52) U.S. Cl.
CPC ....... *A61M 1/962* (2021.05); *A61F 13/00068* (2013.01); *A61F 13/0216* (2013.01);
(Continued)

(58) Field of Classification Search
CPC ..................................................... A61M 1/962
See application file for complete search history.

(56) References Cited

U.S. PATENT DOCUMENTS 3,874,387 A    4/1975  Barbieri
4,224,941 A    9/1980  Stivala
(Continued)

FOREIGN PATENT DOCUMENTS

CN    201664463 U    12/2010
DE    19844355 A1    4/2000
(Continued)

OTHER PUBLICATIONS

International Preliminary Report on Patentability for Application No. PCT/EP2018/079745, dated May 14, 2020, 9 pages.
(Continued)

*Primary Examiner* — Jenna Zhang
(74) *Attorney, Agent, or Firm* — Knobbe, Martens Olson & Bear, LLP

(57) ABSTRACT

Disclosed herein are systems and methods for safe operation of a wound treatment apparatus with electronic components integrated on or within a wound dressing. In some embodiments, the electronic components include a power source, an isolation circuit, a controller, a capacitor, and a negative pressure source. The isolation circuit provides multiple activation states with at least one state preventing applica-
(Continued)

tion of power to the other electronic components capable of storing electrical energy, thereby providing a safe operation of the apparatus. For example, sterilization of the apparatus can be performed safely.

18 Claims, 22 Drawing Sheets

(51) Int. Cl.
    *A61F 13/02* (2006.01)
    *A61L 2/20* (2006.01)
(52) U.S. Cl.
    CPC ........... *A61L 2/206* (2013.01); *A61L 2202/24* (2013.01); *A61M 1/91* (2021.05); *A61M 2205/0233* (2013.01); *A61M 2205/3344* (2013.01); *A61M 2205/6036* (2013.01); *A61M 2205/8237* (2013.01)

(56) References Cited

U.S. PATENT DOCUMENTS

| | | | |
|---|---|---|---|
| 4,398,910 A | 8/1983 | Blake et al. |
| 4,534,356 A | 8/1985 | Papadakis |
| 4,569,674 A | 2/1986 | Phillips et al. |
| 4,624,656 A | 11/1986 | Clark et al. |
| 4,681,562 A | 7/1987 | Beck et al. |
| 4,767,943 A | 8/1988 | Adler et al. |
| 4,979,944 A | 12/1990 | Luzsicza |
| 5,055,195 A | 10/1991 | Trasch et al. |
| 5,055,198 A | 10/1991 | Shettigar |
| 5,056,510 A | 10/1991 | Gilman |
| 5,152,757 A | 10/1992 | Eriksson |
| 5,181,905 A | 1/1993 | Flam |
| 5,266,928 A | 11/1993 | Johnson |
| D357,743 S | 4/1995 | Bilitz et al. |
| 5,527,293 A | 6/1996 | Zamierowski |
| 5,549,584 A | 8/1996 | Gross |
| 5,636,643 A | 6/1997 | Argenta et al. |
| 5,643,189 A | 7/1997 | Masini |
| 5,779,657 A | 7/1998 | Daneshvar |
| 5,833,646 A | 11/1998 | Masini |
| 5,902,256 A | 5/1999 | Benaron |
| 5,964,723 A | 10/1999 | Augustine |
| 6,071,267 A | 6/2000 | Zamierowski |
| 6,142,982 A | 11/2000 | Hunt et al. |
| 6,168,800 B1 | 1/2001 | Dobos et al. |
| 6,183,438 B1 | 2/2001 | Berguer |
| 6,225,523 B1 | 5/2001 | Masini |
| 6,261,276 B1 | 7/2001 | Reitsma |
| 6,261,283 B1 | 7/2001 | Morgan et al. |
| 6,398,767 B1 | 6/2002 | Fleischmann |
| 6,458,109 B1 | 10/2002 | Henley et al. |
| 6,471,982 B1 | 10/2002 | Lydon et al. |
| 6,599,262 B1 | 7/2003 | Masini |
| 6,607,495 B1 | 8/2003 | Skalak et al. |
| 6,683,491 B2 | 1/2004 | Koga et al. |
| 6,685,681 B2 | 2/2004 | Lockwood et al. |
| 6,787,682 B2 | 9/2004 | Gilman |
| 6,794,554 B2 | 9/2004 | Sessions et al. |
| 6,800,074 B2 | 10/2004 | Henley et al. |
| 6,855,135 B2 | 2/2005 | Lockwood et al. |
| 6,942,633 B2 | 9/2005 | Odland |
| 6,951,553 B2 | 10/2005 | Bubb et al. |
| 6,979,324 B2 | 12/2005 | Bybordi et al. |
| 7,004,915 B2 | 2/2006 | Boynton et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,087,806 B2 | 8/2006 | Scheinberg et al. |
| 7,108,683 B2 | 9/2006 | Zamierowski |
| 7,338,482 B2 | 3/2008 | Lockwood et al. |
| 7,361,184 B2 | 4/2008 | Joshi |
| 7,524,315 B2 | 4/2009 | Blott et al. |
| 7,553,306 B1 | 6/2009 | Hunt et al. |
| 7,569,742 B2 | 8/2009 | Haggstrom et al. |
| 7,611,500 B1 | 11/2009 | Lina et al. |
| 7,615,036 B2 | 11/2009 | Joshi et al. |
| D605,775 S | 12/2009 | Koch et al. |
| D608,007 S | 1/2010 | Arbesman et al. |
| 7,645,253 B2 | 1/2010 | Gura et al. |
| 7,687,678 B2 | 3/2010 | Jacobs |
| 7,699,823 B2 | 4/2010 | Haggstrom et al. |
| 7,776,028 B2 | 8/2010 | Miller et al. |
| 7,779,625 B2 | 8/2010 | Joshi et al. |
| D625,422 S | 10/2010 | Arbesman et al. |
| 7,815,616 B2 | 10/2010 | Boehringer et al. |
| 7,837,673 B2 | 11/2010 | Vogel |
| 7,846,141 B2 | 12/2010 | Weston |
| 7,896,864 B2 | 3/2011 | Lockwood et al. |
| 7,922,676 B2 | 4/2011 | Daskal et al. |
| 7,922,703 B2 | 4/2011 | Riesinger |
| 7,942,866 B2 | 5/2011 | Radl et al. |
| 7,959,624 B2 | 6/2011 | Riesinger |
| 7,976,519 B2 | 7/2011 | Bubb et al. |
| 8,007,257 B2 | 8/2011 | Heaton et al. |
| 8,007,481 B2 | 8/2011 | Schuessler et al. |
| 8,062,272 B2 | 11/2011 | Weston |
| 8,062,273 B2 | 11/2011 | Weston |
| 8,080,702 B2 | 12/2011 | Blott et al. |
| 8,092,441 B2 | 1/2012 | Sugito |
| 8,158,844 B2 | 4/2012 | Mcneil |
| 8,167,869 B2 | 5/2012 | Wudyka |
| 8,207,392 B2 | 6/2012 | Haggstrom et al. |
| 8,212,100 B2 | 7/2012 | Moore |
| 8,215,929 B2 | 7/2012 | Shen et al. |
| 8,323,264 B2 | 12/2012 | Weston et al. |
| 8,371,829 B2 | 2/2013 | Jaeb et al. |
| 8,372,049 B2 | 2/2013 | Jaeb et al. |
| 8,372,050 B2 | 2/2013 | Jaeb et al. |
| 8,404,921 B2 | 3/2013 | Lee et al. |
| 8,409,160 B2 | 4/2013 | Locke et al. |
| 8,414,519 B2 | 4/2013 | Hudspeth et al. |
| 8,419,696 B2 | 4/2013 | Wilkes |
| 8,425,478 B2 | 4/2013 | Olson |
| 8,439,894 B1 | 5/2013 | Miller |
| 8,449,508 B2 | 5/2013 | Coulthard et al. |
| 8,460,255 B2 | 6/2013 | Joshi et al. |
| 8,500,776 B2 | 8/2013 | Ebner |
| 8,529,548 B2 | 9/2013 | Blott et al. |
| 8,545,466 B2 | 10/2013 | Andresen et al. |
| 8,579,872 B2 | 11/2013 | Coulthard et al. |
| 8,603,074 B2 | 12/2013 | Kagan |
| 8,604,265 B2 | 12/2013 | Locke et al. |
| 8,641,691 B2 | 2/2014 | Fink et al. |
| 8,641,693 B2 | 2/2014 | Locke et al. |
| 8,702,665 B2 | 4/2014 | Locke et al. |
| 8,764,732 B2 | 7/2014 | Hartwell |
| 8,795,257 B2 | 8/2014 | Coulthard et al. |
| 8,808,274 B2 | 8/2014 | Hartwell |
| 8,814,842 B2 | 8/2014 | Coulthard et al. |
| 8,821,458 B2 | 9/2014 | Locke et al. |
| 8,870,837 B2 | 10/2014 | Locke et al. |
| 8,961,496 B2 | 2/2015 | Locke et al. |
| 8,974,429 B2 | 3/2015 | Gordon et al. |
| 9,061,095 B2 | 6/2015 | Adie et al. |
| 9,084,845 B2 | 7/2015 | Adie et al. |
| 9,089,630 B2 | 7/2015 | Perkins et al. |
| 9,198,802 B2 | 12/2015 | Robinson et al. |
| 9,259,558 B2 | 2/2016 | Tsai |
| 9,265,665 B2 | 2/2016 | Robinson et al. |
| 9,283,118 B2 | 3/2016 | Locke et al. |
| 9,393,354 B2 | 7/2016 | Freedman et al. |
| 9,414,968 B2 | 8/2016 | Heagle |
| 9,421,133 B2 | 8/2016 | Hu et al. |
| 9,427,505 B2 | 8/2016 | Askem et al. |
| 9,452,088 B2 | 9/2016 | Shulman et al. |
| 9,452,245 B2 | 9/2016 | Jaeb et al. |
| 9,560,975 B2 | 2/2017 | Mei et al. |
| D787,690 S | 5/2017 | Mackay et al. |
| 9,737,649 B2 | 8/2017 | Begin et al. |
| 9,770,368 B2 | 9/2017 | Robinson et al. |
| 9,814,811 B2 | 11/2017 | Aalders et al. |

(56) References Cited

U.S. PATENT DOCUMENTS

| | | | |
|---|---|---|---|
| 9,907,703 | B2 | 3/2018 | Allen et al. |
| 9,925,092 | B2 | 3/2018 | Luckemeyer et al. |
| RE46,778 | E | 4/2018 | Peron |
| 9,956,120 | B2 | 5/2018 | Locke |
| 10,004,914 | B2 | 6/2018 | Nettesheim et al. |
| 10,010,656 | B2 | 7/2018 | Jaeb et al. |
| 10,016,544 | B2 | 7/2018 | Coulthard et al. |
| 10,046,095 | B1 | 8/2018 | Middaugh et al. |
| 10,046,096 | B2 | 8/2018 | Askem et al. |
| 10,086,117 | B2 | 10/2018 | Locke et al. |
| 2003/0031586 | A1 | 2/2003 | Eckhardt et al. |
| 2003/0212357 | A1 | 11/2003 | Pace |
| 2004/0076662 | A1 | 4/2004 | Riesinger |
| 2004/0087884 | A1 | 5/2004 | Haddock et al. |
| 2004/0167482 | A1 | 8/2004 | Watson |
| 2005/0012616 | A1 | 1/2005 | Forster et al. |
| 2005/0045461 | A1 | 3/2005 | Sweetland et al. |
| 2005/0065471 | A1 | 3/2005 | Kuntz |
| 2005/0119737 | A1 | 6/2005 | Bene et al. |
| 2005/0137539 | A1 | 6/2005 | Biggie et al. |
| 2006/0029650 | A1 | 2/2006 | Coffey |
| 2006/0086598 | A1 | 4/2006 | Sneek et al. |
| 2006/0107642 | A1 | 5/2006 | Smith et al. |
| 2006/0259102 | A1 | 11/2006 | Slatkine |
| 2007/0055209 | A1 | 3/2007 | Patel et al. |
| 2007/0128055 | A1 | 6/2007 | Lee |
| 2007/0179460 | A1 | 8/2007 | Adahan |
| 2007/0225663 | A1 | 9/2007 | Watt et al. |
| 2007/0255187 | A1 | 11/2007 | Branch |
| 2008/0021356 | A1 | 1/2008 | Castello Escude |
| 2008/0051716 | A1 | 2/2008 | Stutz |
| 2009/0012484 | A1 | 1/2009 | Nielsen et al. |
| 2009/0048556 | A1 | 2/2009 | Durand |
| 2010/0022990 | A1 | 1/2010 | Karpowicz et al. |
| 2010/0100160 | A1 | 4/2010 | Edman et al. |
| 2010/0137775 | A1 | 6/2010 | Hu et al. |
| 2010/0160881 | A1 | 6/2010 | Lin et al. |
| 2010/0280469 | A1 | 11/2010 | Hall et al. |
| 2010/0292632 | A1 | 11/2010 | Mulvihill et al. |
| 2011/0092927 | A1 | 4/2011 | Wilkes et al. |
| 2011/0112492 | A1 | 5/2011 | Bharti et al. |
| 2011/0224631 | A1 | 9/2011 | Simmons et al. |
| 2011/0292623 | A1 | 12/2011 | Stanley |
| 2011/0305736 | A1 | 12/2011 | Wieland et al. |
| 2012/0059294 | A1 | 3/2012 | Schubert et al. |
| 2012/0109034 | A1 | 5/2012 | Locke et al. |
| 2013/0215638 | A1 | 8/2013 | Dabov et al. |
| 2014/0100536 | A1 | 4/2014 | Angel |
| 2014/0343518 | A1 | 11/2014 | Riesinger |
| 2015/0057625 | A1 | 2/2015 | Coulthard |
| 2015/0100045 | A1* | 4/2015 | Allen ............... A61F 13/00068 604/543 |
| 2015/0174304 | A1* | 6/2015 | Askem ............... A61M 1/732 604/319 |
| 2015/0202354 | A1 | 7/2015 | Wall |
| 2016/0015873 | A1 | 1/2016 | Robinson et al. |
| 2016/0166438 | A1 | 6/2016 | Rovaniemi |
| 2016/0199546 | A1 | 7/2016 | Chao |
| 2016/0242964 | A1 | 8/2016 | Rapp et al. |
| 2016/0271305 | A1 | 9/2016 | Kurihara et al. |
| 2016/0361473 | A1 | 12/2016 | Robinson et al. |
| 2017/0112974 | A1 | 4/2017 | Fujisaki |
| 2017/0112975 | A1 | 4/2017 | Fujisaki |
| 2017/0127525 | A1 | 5/2017 | Schonholz |
| 2017/0232189 | A1 | 8/2017 | Qin et al. |
| 2017/0296714 | A1 | 10/2017 | Locke et al. |
| 2017/0319761 | A1 | 11/2017 | Locke et al. |
| 2017/0326277 | A1 | 11/2017 | Huang |
| 2017/0368239 | A1 | 12/2017 | Askem et al. |
| 2018/0008760 | A1 | 1/2018 | Zilbershlag et al. |
| 2018/0021178 | A1 | 1/2018 | Locke et al. |
| 2018/0028728 | A1 | 2/2018 | Aarestad et al. |
| 2018/0104393 | A1 | 4/2018 | Wu et al. |
| 2018/0200414 | A1 | 7/2018 | Askem et al. |
| 2018/0272052 | A1 | 9/2018 | Locke et al. |
| 2018/0296397 | A1 | 10/2018 | Askem et al. |
| 2018/0311078 | A1 | 11/2018 | Hartwell |
| 2018/0318137 | A1 | 11/2018 | Donda et al. |
| 2018/0318165 | A1 | 11/2018 | Donda et al. |
| 2018/0353771 | A1 | 12/2018 | Kim et al. |
| 2019/0021911 | A1 | 1/2019 | Askem et al. |
| 2019/0125943 | A1 | 5/2019 | Askem et al. |
| 2019/0142644 | A1 | 5/2019 | Askem et al. |
| 2019/0143007 | A1 | 5/2019 | Askem et al. |
| 2019/0159938 | A1 | 5/2019 | Askem et al. |
| 2019/0192350 | A1 | 6/2019 | Gowans et al. |
| 2019/0224387 | A1 | 7/2019 | Weston |
| 2019/0282737 | A1 | 9/2019 | Beadle et al. |
| 2020/0022846 | A1 | 1/2020 | Beadle et al. |
| 2021/0001022 | A1 | 1/2021 | Lin |

FOREIGN PATENT DOCUMENTS

| | | |
|---|---|---|
| EP | 0512543 A2 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2340062 B1 | 6/2013 |
| EP | 2603699 A1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2263742 B1 | 9/2013 |
| EP | 1848390 B1 | 12/2013 |
| EP | 1875081 B1 | 12/2013 |
| EP | 2271381 B1 | 12/2013 |
| EP | 2160166 B1 | 1/2014 |
| EP | 1565219 B1 | 2/2014 |
| EP | 2305325 B1 | 4/2014 |
| EP | 2323712 B1 | 4/2014 |
| EP | 2345437 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |

(56) References Cited

FOREIGN PATENT DOCUMENTS

| | | |
|---|---|---|
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 2632613 B1 | 8/2017 |
| EP | 2888478 B1 | 8/2017 |
| EP | 2937107 B1 | 8/2017 |
| EP | 2967627 B1 | 8/2017 |
| EP | 3062751 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2939320 A1 | 6/2010 |
| GB | 2511523 A | 9/2014 |
| RU | 131622 U1 | 8/2013 |
| WO | WO-2009098696 A2 | 8/2009 |
| WO | WO-2009120951 A2 | 10/2009 |
| WO | WO-2011130570 A1 | 10/2011 |
| WO | WO-2011135285 A1 | 11/2011 |
| WO | WO-2011144888 A1 | 11/2011 |
| WO | WO-2012057881 A1 | 5/2012 |
| WO | WO-2014099709 A1 | 6/2014 |
| WO | WO-2016126560 A1 | 8/2016 |
| WO | WO-2017079174 A1 | 5/2017 |
| WO | WO-2017196888 A1 | 11/2017 |
| WO | WO-2018056060 A1 | 3/2018 |
| WO | WO-2018115461 A1 | 6/2018 |
| WO | WO-2018156730 A1 | 8/2018 |
| WO | WO-2018158250 A1 | 9/2018 |
| WO | WO-2018162613 A1 | 9/2018 |
| WO | WO-2018164803 A1 | 9/2018 |
| WO | WO-2018185138 A1 | 10/2018 |
| WO | WO-2018192978 A1 | 10/2018 |
| WO | WO-2018206420 A1 | 11/2018 |
| WO | WO-2019053101 A1 | 3/2019 |
| WO | WO-2019053106 A1 | 3/2019 |
| WO | WO-2019086332 A1 | 5/2019 |
| WO | WO-2019086341 A1 | 5/2019 |
| WO | WO-2019086475 A1 | 5/2019 |
| WO | WO-2019193141 A1 | 10/2019 |

OTHER PUBLICATIONS

International Search Report and Written Opinion for Application No. PCT/EP2018/079745, dated Feb. 13, 2019, 12 pages.

\* cited by examiner

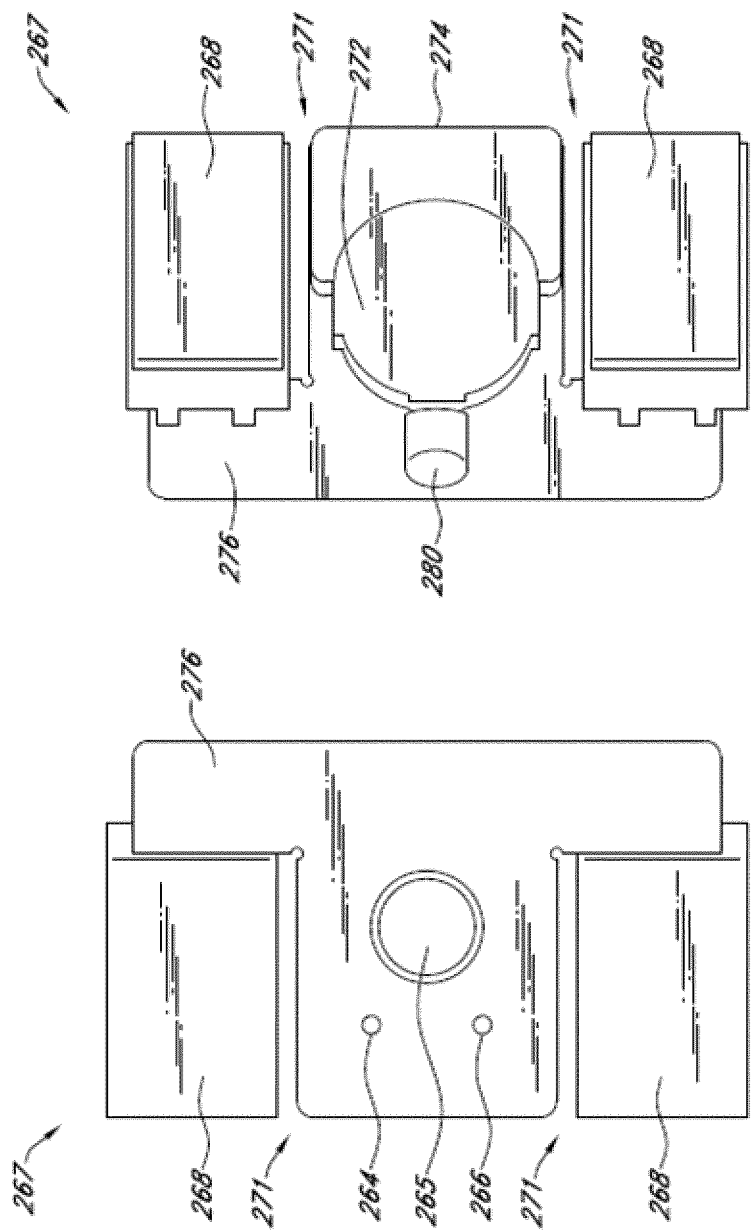

SAFE OPERATION OF INTEGRATED NEGATIVE PRESSURE WOUND TREATMENT APPARATUSES

This application is a U.S. national stage application of International Patent Application No. PCT/EP2018/079745, entitled "SAFE OPERATION OF INTEGRATED NEGATIVE PRESSURE WOUND TREATMENT APPARATUSES," filed Oct. 30, 2018, which claims priority to Great Britain Patent Application No. 1718054.8, filed on Nov. 1, 2017 which is hereby incorporated by reference in their entireties and made part of this disclosure.

BACKGROUND

Technical Field

Embodiments described herein relate to apparatuses, systems, and methods related to treatment of wounds, for example using dressing in combination with negative pressure wound therapy.

Description of the Related Art

The treatment of open or chronic wounds that are too large to spontaneously close or otherwise fail to heal by means of applying negative pressure to the site of the wound is well known in the art. Negative pressure wound therapy (NPWT) systems currently known in the art commonly involve placing a cover that is impermeable or semi-permeable to fluids over the wound, using various means to seal the cover to the tissue of the patient surrounding the wound, and connecting a source of negative pressure (such as a vacuum pump) to the cover in a manner so that negative pressure is created and maintained under the cover. It is believed that such negative pressures promote wound healing by facilitating the formation of granulation tissue at the wound site and assisting the body's normal inflammatory process while simultaneously removing excess fluid, which may contain adverse cytokines and/or bacteria. However, further improvements in NPWT are needed to fully realize the benefits of treatment.

Many different types of wound dressing are known for aiding in NPWT systems. These different types of wound dressing include many different types of materials and layers, for example, gauze, pads, foam pads or multi-layer wound dressing. One example of a multi-layer wound dressing is the PICO dressing, available from Smith & Nephew, which includes a superabsorbent layer beneath a backing layer to provide a canister-less system for treating a wound with NPWT. The wound dressing may be sealed to a suction port providing connection to a length of tubing, which may be used to pump fluid out of the dressing and/or to transmit negative pressure from a pump to the wound dressing.

Prior art dressing for use in negative pressure such as those described above have included a negative pressure source located in a remote location from the wound dressing. Negative pressure sources located remote from the wound dressing have to be held by or attached to the user or other pump support mechanism. Additionally, a tubing or connector is required to connect the remote negative pressure source to the wound dressing. The remote pump and tubing can be cumbersome and difficult to hide in or attach to patient clothing. Depending on the location of the wound dressing, it can be difficult to comfortably and conveniently position the remote pump and tubing. When used, wound exudate may soak into the dressing, and the moisture from the wound has made it difficult to incorporate electronic components into the dressing.

SUMMARY

In some embodiments, a negative pressure wound therapy system includes a wound dressing configured to be placed over a wound of a patient, a source of negative pressure disposed on or within the dressing, the source of negative pressure configured to provide negative pressure to the wound, and an electronic circuit disposed on or within the dressing. The electronic circuit can include a controller configured to operate the source of negative pressure, a power source configured to supply power to the electronic circuit, and an isolation circuit in electrical communication with the power source and the controller. The isolation circuit can be configured to operate in a first state in which the isolation circuit prevents application of power to the controller and in a second state in which the isolation circuit permits application of power to the controller. The isolation circuit can include an activation switch configured to be activated and to cause the isolation circuit to operate in the second state.

The system of the preceding paragraph can include one or more of the following features. The activation switch can be activated by a tab configured to be removed by a user, wherein activation of the activation switch can cause the isolation circuit to operate in the second state. The activation switch can be configured to remain activated following removal of the tab. The tab can include conductive material configured to be applied to the activation switch to activate the activation switch. The conductive material can include silver ink deposited in a region of the tab, and the region can be configured to be in contact with the activation switch during activation. The region can be configured to make electrical contact. The activation switch can be a button. The electronic circuit can include at least one capacitor configured to store energy supplied by the power source and provide the stored energy to the source of negative pressure. The isolation circuit in the first state of operation can be further configured to prevent charging of the at least one capacitor. The electronic circuit can further comprise an operation switch configured to activate and pause provision of negative pressure by the source of negative pressure. The isolation circuit can include a latching circuit. The power source can be non-removable. The source of negative pressure can be a micropump.

The system of any of preceding paragraphs can include one or more of the following features. The electronic circuit can be configured to not activate provision of negative pressure by the source of negative pressure when the isolation circuit is in the first state and the operation switch is activated. The latching circuit can be configured to cause the isolation circuit to remain in the second state in response to an initial activation of the activation switch. The latching circuit can be configured to cause the isolation circuit to remain in the second state in response to deactivation of the activation switch subsequent to the initial activation. The electronic circuit can be configured to not activate provision of negative pressure by the source of negative pressure when the isolation circuit is in the first state. The system can include an indicator configured to provide at least one of an indication that the activation switch has not been activated or an indication that the activation switch has been activated. The controller can include a boost converter configured to power the source of negative pressure, and the system can include a primary controller configured to be powered by the power source when the isolation circuit is in the first or second state. The system can include at least one energy storing element and can be configured to store energy supplied by the boost converter and power the source of negative pressure with the stored energy.

In some embodiments, a method of operating a negative pressure wound therapy apparatus that includes a wound dressing, a source of negative pressure disposed on or within the wound dressing, and an electronic circuit disposed on or within the wound dressing and configured to operate the source of negative pressure includes activating an activation switch configured to cause the electronic circuit to operate in a first state in which power is applied to a controller of the electronic circuit, wherein the apparatus has been sterilized with Ethylene oxide (EtO) while the electronic circuit was operating in a second state in which no power was applied to the controller, positioning the wound dressing over the wound of the patient, and activating the source of negative pressure to provide negative pressure to the wound.

The method of the preceding paragraph can include one or more of the following features. Activating the activation switch can be performed by removing a tab. The activation switch can be a button. Activating the source of negative pressure can include activating an operation switch configured to activate and pause the source of negative pressure.

In some embodiments, a method of operating a negative pressure wound therapy apparatus that includes a wound dressing, a source of negative pressure disposed on or within the wound dressing, and an electronic circuit disposed on or within the wound dressing and configured to operate the source of negative pressure includes activating an activation switch configured to cause the electronic circuit to operate in a first state in which power is applied to a controller of the electronic circuit, wherein the apparatus has been sterilized with Ethylene oxide (EtO) while the electronic circuit was operating in a second state in which no power was applied to the controller and activating the source of negative pressure to provide negative pressure to a wound dressing.

The method of any of the preceding paragraphs can include one or more of the following features. Activating the activation switch can be performed by removing a tab. The activation switch can be a button, and activating the activation switch can be performed by pressing the button. Activating the source of negative pressure can include activating an operation switch configured to activate and pause the source of negative pressure.

In some embodiments, a method of operating a negative pressure wound therapy apparatus including a wound dressing, a source of negative pressure disposed on or within the wound dressing, and an electronic circuit disposed on or within the wound dressing and configured to operate the source of negative pressure includes maintaining an isolation circuit of the electronic circuit in an inactive state during which no power is supplied to an energy storing component of the electronic circuit configured to supply power to the source of negative pressure, wherein the apparatus is sterilized when the isolation circuit is in the inactive state, in response to activation of an activation switch of the electronic circuit, transitioning the isolation circuit to an active state during which power is supplied to the energy storing component, and activating the source of negative pressure when the isolation circuit is in the second state. The apparatus can be sterilized with Ethylene oxide (EtO).

The method of any of the preceding paragraphs can include one or more of the following features. The method can include maintaining the isolation circuit in the active state in response to an initial activation of the activation switch. Activation of the activation switch can include at least one of pulling a tab, pressing a button, or connecting a secondary power source. Activating the source of negative pressure can include activating the source of negative pressure in response to an activation of an operation switch. The method can include deactivating the source of negative pressure in response to a deactivation of the operation switch. The method can include not activating the source of negative pressure in response to the activation of the operation switch when the isolation circuit is in the inactive state. The method can include indicating at least one of that the activation switch has not been activated or that the activation switch has been activated. The energy storing component can be a capacitor.

In some embodiments, a negative pressure wound therapy apparatus includes a wound dressing, a source of negative pressure disposed on or within the wound dressing, and an electronic circuit disposed on or within the wound dressing and configured to operate the source of negative pressure. The activation circuit can include an isolation circuit configured to be maintained in an inactive state during which no power is supplied to an energy storing component of the electronic circuit configured to supply power to the source of negative pressure, wherein the apparatus is sterilized when the isolation circuit is in the inactive state. The isolation circuit can be further configured to, in response to activation of an activation switch of the electronic circuit, transition to an active state during which power is supplied to the energy storing component.

The apparatus of any of the preceding paragraphs can include one or more of the following features. The apparatus can be sterilized with Ethylene oxide (EtO). The isolation circuit can be further configured to remain in the active state in response to an initial activation of the activation switch. Activation of the activation switch can include at least one of pulling a tab, pressing a button, or connecting a secondary power source. Activation of the source of negative pressure can be performed (for example, by the electronic circuit) in response to an activation of an operation switch. Deactivation of the source of negative pressure can be performed (for example, by the electronic circuit) in response to a deactivation of the operation switch. The electronic circuit can be configured to not activate the source of negative pressure in response to the activation of the operation switch when the isolation circuit is in the inactive state. The electronic circuit can be configured to indicate at least one of that the activation switch has not been activated or that the activation switch has been activated. The energy storing component can include a capacitor.

Any of the features, components, or details of any of the arrangements or embodiments disclosed in this application, including without limitation any of the pump embodiments and any of the negative pressure wound therapy embodiments disclosed below, are interchangeably combinable with any other features, components, or details of any of the arrangements or embodiments disclosed herein to form new arrangements and embodiments.

BRIEF DESCRIPTION OF THE DRAWINGS

Features and advantages of the present disclosure will be apparent from the following detailed description, taken in conjunction with the accompanying drawings of which:

FIGS. 2A-2B illustrate embodiments of an electronics unit incorporated into a wound dressing.

DETAILED DESCRIPTION

Figure 1A:
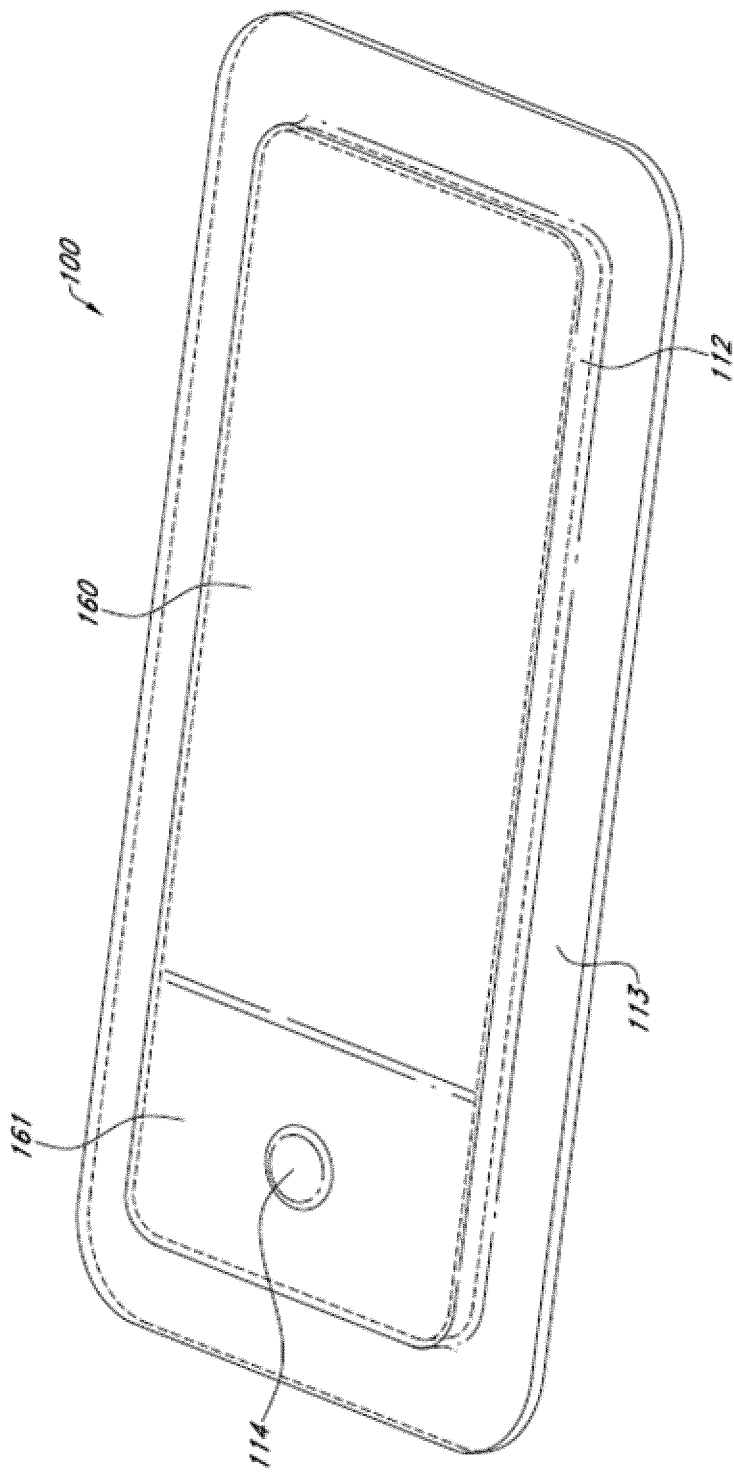
FIGS. 1A-1C illustrates a wound dressing incorporating the source of negative pressure and/or other electronic components within the wound dressing.

Embodiments disclosed herein relate to apparatuses and methods of treating a wound with reduced pressure, including a source of negative pressure and wound dressing components and apparatuses. The apparatuses and components comprising the wound overlay and packing materials, if any, are sometimes collectively referred to herein as dressing.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable to use in topical negative pressure ("TNP") therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753, 894, titled "Wound cleansing apparatus with stress," issued Jul. 13, 2010. The disclosures of both of these patents are hereby incorporated by reference in their entirety.

International Application PCT/GB2012/000587, titled "WOUND DRESSING AND METHOD OF TREATMENT" and filed on Jul. 12, 2012, and published as WO 2013/007973 A2 on Jan. 17, 2013, is an application, hereby incorporated and considered to be part of this specification, that is directed to embodiments, methods of manufacture, and wound dressing components and wound treatment apparatuses that may be used in combination or in addition to the embodiments described herein. Additionally, embodiments of the wound dressing, wound treatment apparatuses and methods described herein may also be used in combination or in addition to those described in International Application No. PCT/IB2013/001469, filed May 22, 2013, titled "APPARATUSES AND METHODS FOR NEGATIVE PRESSURE WOUND THERAPY," published as WO 2013/175306 on Nov. 28, 2013, U.S. patent application Ser. No. 14/418874, filed Jan. 30, 2015, published as U.S. Publication No. 2015/0216733, published Aug. 6, 2015, titled "WOUND DRESSING AND METHOD OF TREATMENT," U.S. patent application Ser. No. 14/418908, filed Jan. 30, 2015, published as U.S. Publication No. 2015/0190286, published Jul. 9, 2015, titled "WOUND DRESSING AND METHOD OF TREATMENT," U.S. patent application Ser. No. 14/658,068, filed Mar. 13, 2015, U.S. application Ser. No. 2015/0182677, published Jul. 2, 2015, titled "WOUND DRESSING AND METHOD OF TREATMENT," the disclosures of which are hereby incorporated by reference in their entireties. Embodiments of the wound dressing, wound treatment apparatuses and methods described herein may also be used in combination or in addition to those described in U.S. patent application Ser. No. 13/092,042, filed Apr. 21 2011, published as U.S. 2011/0282309, titled "WOUND DRESSING AND METHOD OF USE," and which is hereby incorporated by reference in its entirety, including further details relating to embodiments of wound dressing, the wound dressing components and principles, and the materials used for the wound dressing.

Figure 1B:
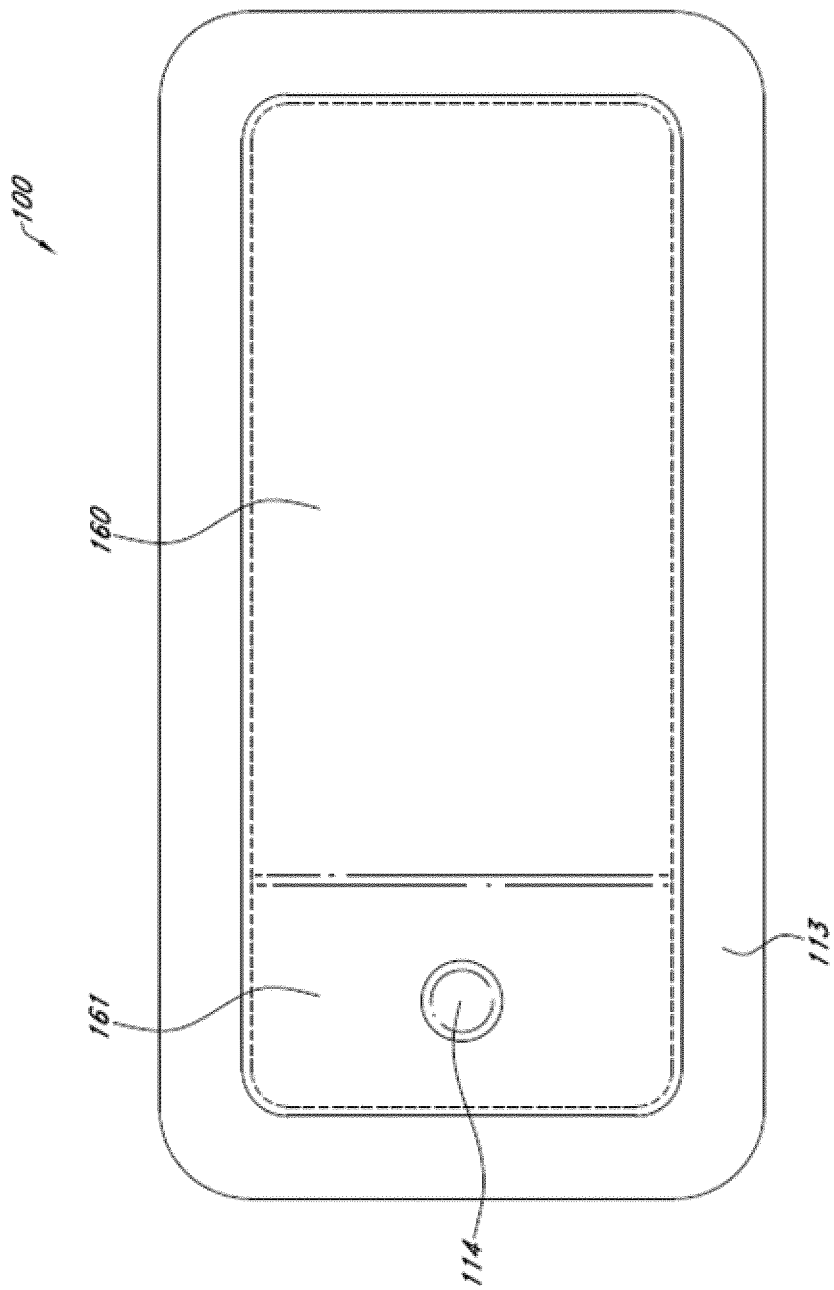
Figure 1C:
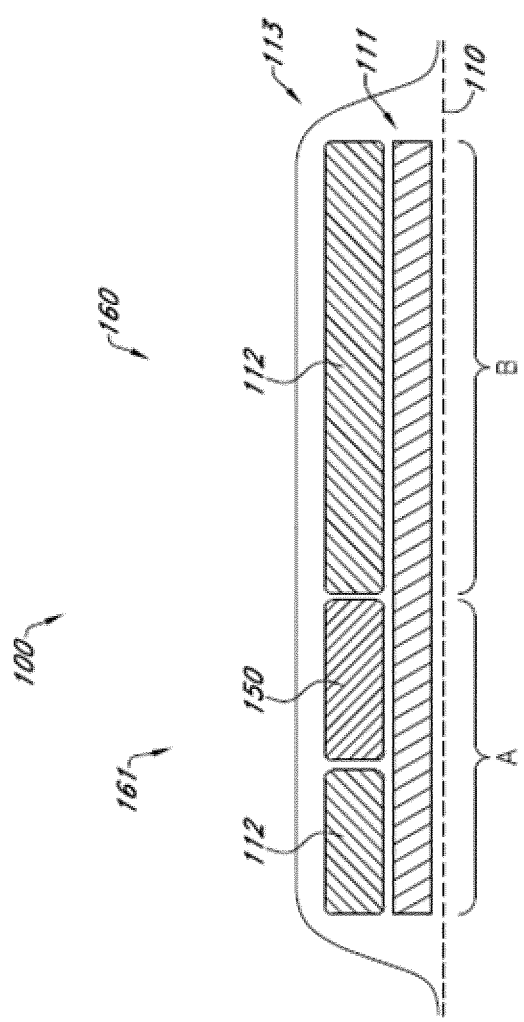

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. The wound dressing can include various material layers described here and described in further detail in International Application No. PCT/EP2017/055225, filed Mar. 6, 2017, entitled WOUND TREATMENT APPARATUSES AND METHODS WITH NEGATIVE PRESSURE SOURCE INTEGRATED INTO WOUND DRESSING. The material layers can include a wound contact layer, one or more absorbent layers, one or more transmission or spacer layers, and a backing layer or cover layer covering the one or more absorbent and transmission or spacer layers. The wound dressing can be placed over a wound and sealed to the wound with the pump and/or other electronic components contained under the cover layer within the wound dressing. In some embodiments, the dressing can be provided as a single article with all wound dressing elements (including the pump) pre-attached and integrated into a single unit. In some embodiments, a periphery of the wound contact layer can be attached to the periphery of the cover layer enclosing all wound dressing elements as illustrated in FIGS. 1A-1C.

In some embodiments, the pump and/or other electronic components can be configured to be positioned adjacent to or next to the absorbent and/or transmission layers so that the pump and/or other electronic components are still part of a single article to be applied to a patient. In some embodiments, with the pump and/or other electronics positioned away from the wound site. FIGS. 1A-1C illustrates a wound dressing incorporating the source of negative pressure and/or other electronic components within the wound dressing. FIGS. 1A-1C illustrates a wound dressing 100 with the pump and/or other electronics positioned away from the wound site. The wound dressing can include an electronics area 161 and an absorbent area 160. The dressing can comprise a wound contact layer 110 (not shown in FIGS. 1A-1B) and a moisture vapor permeable film or cover layer 113 positioned above the contact layer and other layers of the dressing. The wound dressing layers and components of the electronics area as well as the absorbent area can be covered by one continuous cover layer 113 as shown in FIGS. 1A-1C.

The dressing can comprise a wound contact layer 110, a transmission layer 111, an absorbent layer 112, a moisture vapor permeable film or cover layer 113, 113 positioned above the wound contact layer, transmission layer, absorbent layer, or other layers of the dressing. The wound contact layer can be configured to be in contact with the wound. The wound contact layer can include an adhesive on the patient facing side for securing the dressing to the surrounding skin or on the top side for securing the wound contact layer to a cover layer or other layer of the dressing. In operation, the wound contact layer can be configured to provide unidirectional flow so as to facilitate removal of exudate from the wound while blocking or substantially preventing exudate from returning to the wound.

The wound contact layer 110 can be a polyurethane layer or polyethylene layer or other flexible layer which is perforated, for example via a hot pin process, laser ablation process, ultrasound process or in some other way or otherwise made permeable to liquid and gas. The wound contact layer 110 has a lower surface and an upper surface. The perforations preferably comprise through holes in the wound contact layer 110 which enable fluid to flow through the layer 110. The wound contact layer 110 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 110 may help maintain the integrity of the entire dressing 100 while also creating an air tight seal around the absorbent pad in order to maintain negative pressure at the wound.

Some embodiments of the wound contact layer 110 may also act as a carrier for an optional lower and upper adhesive layer (not shown). For example, a lower pressure sensitive adhesive may be provided on the lower surface of the wound dressing 100 whilst an upper pressure sensitive adhesive layer may be provided on the upper surface of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized it may be helpful to adhere the wound dressing 100 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A layer 111 of porous material can be located above the wound contact layer 110. As used herein, the terms porous material, spacer, and/or transmission layer can be used interchangeably to refer to the layer of material in the dressing configured to distribute negative pressure throughout the wound area. This porous layer, or transmission layer, 111 allows transmission of fluid including liquid and gas away from a wound site into upper layers of the wound dressing. In particular, the transmission layer 111 preferably ensures that an open air channel can be maintained to communicate negative pressure over the wound area even when the absorbent layer has absorbed substantial amounts of exudates. The layer 111 should preferably remain open under the typical pressures that will be applied during negative pressure wound therapy as described above, so that the whole wound site sees an equalized negative pressure. The layer 111 may be formed of a material having a three dimensional structure. For example, a knitted or woven spacer fabric (for example Baltex 7970 weft knitted polyester) or a non-woven fabric could be used.

The transmission layer assists in distributing negative pressure over the wound site and facilitating transport of wound exudate and fluids into the wound dressing. In some embodiments, the transmission layer can be formed at least partially from a three dimensional (3D) fabric.

In some embodiments, the transmission layer 111 comprises a 3D polyester spacer fabric layer including a top layer (that is to say, a layer distal from the wound-bed in use) which is a 84/144 textured polyester, and a bottom layer (that is to say, a layer which lies proximate to the wound bed in use) which is a 10 denier flat polyester and a third layer formed sandwiched between these two layers which is a region defined by a knitted polyester viscose, cellulose or the like monofilament fiber. Other materials and other linear mass densities of fiber could of course be used.

Whilst reference is made throughout this disclosure to a monofilament fiber it will be appreciated that a multistrand alternative could of course be utilized. The top spacer fabric thus has more filaments in a yarn used to form it than the number of filaments making up the yarn used to form the bottom spacer fabric layer.

This differential between filament counts in the spaced apart layers helps control moisture flow across the transmission layer. Particularly, by having a filament count greater in the top layer, that is to say, the top layer is made from a yarn having more filaments than the yarn used in the bottom layer, liquid tends to be wicked along the top layer more than the bottom layer. In use, this differential tends to draw liquid away from the wound bed and into a central region of the dressing where the absorbent layer 112 helps lock the liquid away or itself wicks the liquid onwards towards the cover layer 113 where it can be transpired.

Preferably, to improve the liquid flow across the transmission layer 111 (that is to say perpendicular to the channel region formed between the top and bottom spacer layers), the 3D fabric may be treated with a dry cleaning agent (such as, but not limited to, Perchloro Ethylene) to help remove any manufacturing products such as mineral oils, fats or waxes used previously which might interfere with the hydrophilic capabilities of the transmission layer. In some embodiments, an additional manufacturing step can subsequently be carried in which the 3D spacer fabric is washed in a hydrophilic agent (such as, but not limited to, Feran Ice 30 g/l available from the Rudolph Group). This process step helps ensure that the surface tension on the materials is so low that liquid such as water can enter the fabric as soon as it contacts the 3D knit fabric. This also aids in controlling the flow of the liquid insult component of any exudates.

Further, an absorbent layer (such as layer 112) for absorbing and retaining exudate aspirated from the wound can be utilized. In some embodiments, a superabsorbent material can be used in the absorbent layer 112. In some embodiments, the absorbent includes a shaped form of a superabsorber layer.

A layer 112 of absorbent material is provided above the transmission layer 111. The absorbent material, which comprise a foam or non woven natural or synthetic material, and which may optionally comprise a super-absorbent material, forms a reservoir for fluid, particularly liquid, removed from the wound site. In some embodiments, the layer 111 may also aid in drawing fluids towards the cover layer 113.

The material of the absorbent layer 112 may also prevent liquid collected in the wound dressing from flowing freely within the dressing, and preferably acts so as to contain any liquid collected within the dressing. The absorbent layer 112 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 112 may typically be manufactured from ALLEVYN™ foam, Freudenberg 114-224-4 or Chem-Posite™ 11C-450. In some embodiments, the absorbent layer 112 may comprise a composite comprising superabsorbent powder, fibrous material such as cellulose, and bonding fibers. In a preferred embodiment, the composite is an airlaid, thermally-bonded composite.

In some embodiments, the absorbent layer 112 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

The wound dressing layers of the electronics area and the absorbent layer can be covered by one continuous cover layer or backing layer 113. As used herein, the terms cover layer and/or backing layer can be used interchangeably to refer to the layer of material in the dressing configured to cover the underlying dressing layers and seal to the wound contact layer and/or the skin surrounding the wound. In some embodiments, the cover layer can include a moisture vapor permeable material that prevents liquid exudate removed from the wound and other liquids from passing through, while allowing gases through.

The cover layer 113 is preferably gas impermeable, but moisture vapor permeable, and can extend across the width of the wound dressing 100. The cover layer 113, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way an effective chamber is made between the cover layer 113 and a wound site where a negative pressure can be established. The cover layer 113 is preferably sealed to the wound contact layer 110 in a border region around the circumference of the dressing, ensuring that no air is drawn in through the border area, for example via adhesive or welding techniques. The cover layer 113 protects the wound from external bacterial contamination (bacterial barrier) and allows liquid from wound exudates to be transferred through the layer and evaporated from the film outer surface. The cover layer 113 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the cover layer increases when the cover layer becomes wet. The moisture vapor permeability of the wet cover layer may be up to about ten times more than the moisture vapor permeability of the dry cover layer.

The electronics area 161 can include a source of negative pressure (such as a pump) and some or all other components of the TNP system, such as power source(s), sensor(s), connector(s), user interface component(s) (such as button(s), switch(es), speaker(s), screen(s), etc.) and the like, that can be integral with the wound dressing. For example, the electronics area 161 can include a button or switch 114 as shown in FIGS. 1A-1B. The button or switch 114 can be used for operating the pump (e.g., turning the pump on/off).

The absorbent area 160 can include an absorbent material 112 and can be positioned over the wound site. The electronics area 161 can be positioned away from the wound site, such as by being located off to the side from the absorbent area 160. The electronics area 161 can be positioned adjacent to and in fluid communication with the absorbent area 160 as shown in FIGS. 1A-1C. In some embodiments, each of the electronics area 161 and absorbent area 160 may be rectangular in shape and positioned adjacent to one another. In FIG. 1C, the electronics area 161 is noted as area "A" and the absorbent area 160 is noted as area "B". In some embodiments, as illustrated in FIG. 1C, electronic components 150 can be positioned within a recess or cut out of the absorbent material 112 but off to the side of the absorbent area. As shown in the cross sectional view of the wound dressing layers in FIG. 1C, the absorbent material 112 can be positioned on both sides of the electronic components 150.

In some embodiments, additional layers of dressing material can be included in the electronics area 161, the absorbent area 160, or both areas. In some embodiments, the dressing can comprise one or more transmission or spacer layers and/or one or more absorbent layer positioned above the wound contact layer 110 and below the cover layer 113 of the dressing.

In some embodiments, the electronics area 161 of the dressing can comprise electronic components 150. In some embodiments, the electronics area 161 of the dressing can comprise one or more layers of transmission or spacer material and/or absorbent material and electronic components 150 can be embedded within the one or more layers of transmission or spacer material and/or absorbent material. The layers of transmission or absorbent material can have recesses or cut outs to embed the electronic components 150 within whilst providing structure to prevent collapse. The electronic components 150 can include a pump, power source, controller, and/or an electronics package.

A pump exhaust can be provided to exhaust air from the pump to the outside of the dressing. The pump exhaust can be in communication with the electronics area 161 and the outside of the dressing.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound. Additionally, the layers can have a proximal wound-facing face referring to a side or face of the layer closest to the skin or wound and a distal face referring to a side or face of the layer furthest from the skin or wound.

FIGS. 1A-1C illustrates a wound dressing apparatus incorporating the pump and/or other electronic components within the wound dressing and offset from the absorbent layer. In some embodiments, as shown in FIG. 1C, the absorbent area 160 comprises a transmission layer 111 positioned above the wound contact layer 110. An absorbent layer 112 can be provided above the transmission layer 111. In some embodiments, the electronics area 161 can include an electronics unit (shown in FIGS. 2A-2B). In some embodiments, the electronics unit is provided directly over the wound contact layer. In other embodiments, the electronics unit can be placed above a layer of wicking material, absorbent material, or transmission material that sits above the wound contact layer 110 of the dressing. For example, as shown in FIG. 1C, the electronics unit 150 may be positioned over the transmission layer 111. In some embodiments, the transmission layer 111 can be a single layer of material extending below the electronics unit 150 and the absorbent material 112. Thus, in some embodiments, the transmission layer 111 extends continuously through the absorbent area 160 and the electronics area 161. In alternative embodiments, the transmission layer below the electronics unit can be a different transmission layer than the transmission layer below the absorbent material 112. The transmission layer 111, absorbent material 112, and electronics unit 150 can be covered with a cover layer 113 that seals to a perimeter of the wound contact layer 110 as shown in FIGS. 1A-1C.

The electronics area 161 can include an electronics unit 150 positioned below the cover layer 113 of the dressing. In some embodiments, the electronics unit can be surrounded by a material to enclose or encapsulate a negative pressure source and electronics components by surrounding the electronics. In some embodiments, this material can be a casing. In some embodiments, the electronics unit can be encapsulated or surrounded by a protective coating, for example, a hydrophobic coating as described herein. The electronics unit can be in contact with the dressing layers in the absorbent area 160 and covered by the cover layer 113. As used herein, the electronics unit includes a lower or wound facing surface that is closest to the wound and an opposite, upper surface, furthest from the wound when the wound dressing is placed over a wound.

FIG. 1C illustrates an embodiment of a wound dressing incorporating an electronics unit 150 within the dressing. In some embodiments, the electronics sub assembly or electronics unit 150 can be embedded in an aperture or hole in an absorbent layer 112 towards one end of the dressing, as depicted in FIG. 1C.

In some embodiments, the absorbent components and electronics components can be overlapping but offset. For example, a portion of the electronics area can overlap the absorbent area, for example overlapping the superabsorber layer, but the electronics area is not completely over the absorbent area. Therefore, a portion of the electronics area can be offset from the absorbent area. The dressing layer and electronic components can be enclosed in a wound contact layer 110 positioned below the lower most layer and a cover layer 113 positioned above the absorbent layer 112 and electronics 150. The wound contact layer 110 and cover layer 113 can be sealed at a perimeter enclosing the dressing components. In some embodiments, the cover layer can be in direct physical contact with the absorbent material, and/or the electronics unit. In some embodiments, the cover layer can be sealed to a portion of the electronics unit and/or casing, for example, in areas where holes or apertures are used to accommodate the electronic components (e.g. a switch and/or exhaust).

FIGS. 2A-2B illustrate embodiments of an electronics unit 267 that can be incorporated into a wound dressing. FIG. 2A illustrates the top view of the electronics unit. FIG. 2B illustrates a bottom or wound facing surface of the electronics unit. The electronics unit 267 can include a pump 272 and one or more batteries 268. The electronics unit 267 can include a flexible circuit board 276 configured to be in electrical communication with the pump 272 and/or batteries 268.

As illustrated in FIG. 2A, the electronics unit 267 can include single button or switch 265 on the upper surface of the unit. The single button or switch 265 can be used as an on/off button or switch to stop and start operation of the pump and/or electronic components. The switch 265 can be a dome type switch configured to sit on the top of the pump. Because the switch is situated within the dressing the cover layer can be easily sealed around or over the switch. In some embodiments, the cover layer can have an opening or hole positioned above the switch. The cover layer can be sealed to the outer perimeter of the switch 265 to maintain negative pressure under the wound cover. The switch can be placed on any surface of the electronics unit and can be in electrical connection with the pump.

The electronics unit 267 can also include one or more vents or exhausts aperture 264 on the flexible circuit board for expelling the air exhausted from the pump. As shown in FIG. 2B, a pump outlet exhaust mechanism 274 can be attached to the outlet of the pump 272. The vent or exhaust aperture 264 can be in fluid communication with a pump exhaust mechanism 274 positioned at the outlet of the pump and extending to the lower surface of the flexible circuit board. In some embodiments, an exhaust vent 264 on the flexible circuit board can provide communication with the top surface of the dressing and allow the pump exhaust to be vented from the electronics unit. In some embodiments, the exhaust mechanism 274 can be attached to the outlet end of the pump and can extend out from the pump at a 90-degree angle from the pump orientation to communicate with the bottom surface of the flexible circuit board. In some embodiments, the exhaust mechanism 274 can include an antibacterial membrane and/or a non-return valve. In some embodiments, the exhaust vent 264 can include an antibacterial membrane and/or a non-return valve. The exhausted air from the pump can pass through the pump outlet and exhaust mechanism 274. In some embodiments, the cover layer 113 can include apertures or holes positioned above the exhaust vent 264 and/or membrane. The cover layer 113 can be sealed to the outer perimeter of the exhaust 264 to maintain negative pressure under the wound cover 113. In some embodiments, the exhausted air can be exhausted through the gas permeable material or moisture vapor permeable material of the cover layer. In some embodiments, the cover layer does not need to contain apertures or holes over the exhaust and the exhausted air is expelled through the cover layer. In some embodiments, the pump outlet mechanism 274 can be a custom part formed to fit around the pump as shown in FIG. 2B. The electronic unit 267 can include a pump inlet protection mechanism 280 as shown in FIG. 2C positioned on the portion of the electronic unit closest to the absorbent area and aligned with the inlet of the pump 272. The pump inlet protection mechanism 280 is positioned between the pump inlet and the absorbent area or absorbent layer of the dressing. The pump inlet protection mechanism 280 can be formed of a hydrophobic material to prevent fluid from entering the pump 272.

In some embodiments, the upper surface of the electronics unit can include one or more indicators 266 for indicating a condition of the pump and/or level of pressure within the dressing. The indicators can be small LED lights or other light source that are visible through the dressing components or through holes in the dressing components above the indicators. The indicators can be green, yellow, red, orange, or any other color. For example, there can be two lights, one green light and one orange light. The green light can indicate the device is working properly and the orange light can indicate that there is some issue with the pump (e.g. dressing leak, saturation level of the dressing, and/or low battery).

FIGS. 2A-2B illustrates an embodiment of an electronics unit 267. The electronics unit 267 can include a pump 272 and one or more batteries 268 or other power source to power the pump 272 and other electronics. The pump can operate at about 27 volts or about 30 volts. The two batteries can allow for a more efficient voltage increase (6 volts to 30 volts) than would be possible with a single battery.

The batteries 268 can be in electrical communication with a flexible circuit board 276. In some embodiments, one or more battery connections are connected to a surface of the flexible circuit board 276. In some embodiments, the flexible circuit board can have other electronics incorporated within. For example, the flexible circuit board may have various sensors including, but not limited to, one or more pressure sensors, temperature sensors, optic sensors and/or cameras, and/or saturation indicators.

In such embodiments, the components of the electronics unit 267 may include a protective coating to protect the electronics from the fluid within the dressing. The coating can provide a means of fluid separation between the electronics unit 267 and the absorbent materials of the dressing. The coating can be a hydrophobic coating including, but not limited to, a silicone coating or polyurethane coating. In some embodiments, the electronics unit 267 can be encapsulated in a protective housing or enclosure as described in more detail herein. The pump inlet component can be used to protect the pump from fluid on the inlet and the pump outlet mechanism can include a non-return valve that protects fluid from entering the outlet as described in more detail with reference to PCT International Application No. PCT/EP2017/055225, filed Mar. 6, 2017, titled WOUND TREATMENT APPARATUSES AND METHODS WITH NEGATIVE PRESSURE SOURCE INTEGRATED INTO WOUND DRESSING and PCT International Application No. PCT/EP2017/059883, filed Apr. 26, 2017, titled WOUND DRESSING AND METHODS OF USE WITH INTEGRATED NEGATIVE PRESSURE SOURCE HAVING A FLUID INGRESS INHIBITION COMPONENT, which are hereby incorporated by reference in their entireties.

The electronics unit 267 includes one or more slits, grooves or recesses 271 in the unit between the pump and the two batteries. The slits, grooves or recesses 271 can allow for the electronics unit 267 to be flexible and conform to the shape of the wound. The unit 267 can have two parallel slits, grooves or recesses 271 forming three segments of the electronics unit 267. The slits, grooves or recesses 271 of the unit 267 create hinge points or gaps that allows for flexibility of the electronics unit at that hinge point. The pump exhaust vent 264, switch 265, and indicator 266 are shown on the top surface of the electronics unit 267. As illustrated, one embodiment of the electronics unit 267 has two hinge points to separate the unit into three regions or panels, for example one to contain one battery, one to contain the pump, and one to contain another battery. In some embodiments, the slits, grooves or recesses may extend parallel with a longitudinal axis of the dressing that extends along the length of the dressing through the electronics area of the dressing through the absorbent area of the dressing.

Figure 3A:
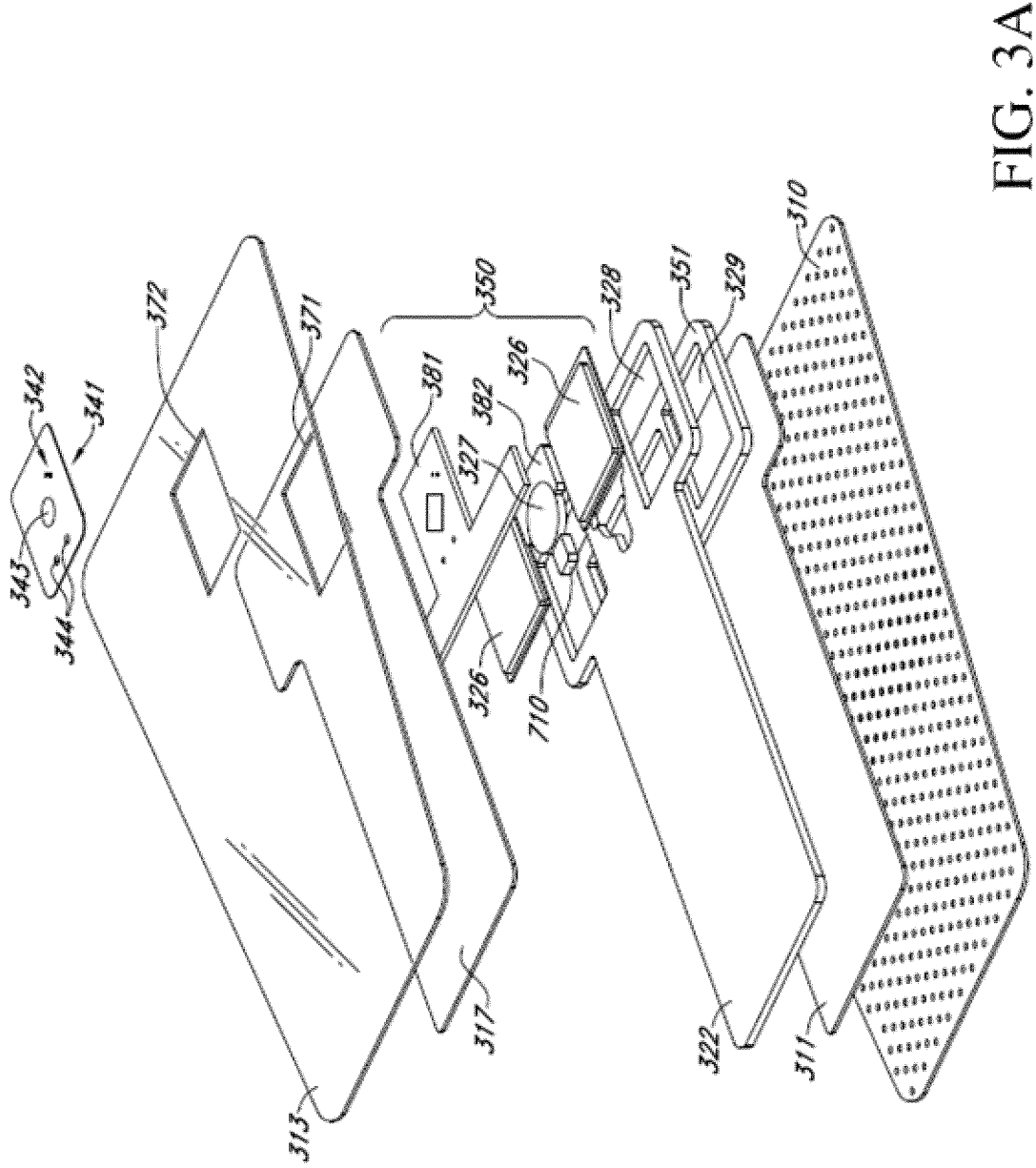
FIG. 3A illustrates an embodiment of wound dressing layers incorporating the electronic components within the wound dressing.

FIG. 3A illustrates an embodiment of wound dressing layers incorporating the electronic components within the wound dressing. FIG. 3A illustrates a wound dressing with a wound contact layer 310 configured to contact the wound. A transmission layer or spacer layer 311 is provided over the wound contact layer. The transmission layer 311 can assist in transmitting and distributing negative pressure over the wound site.

A first layer of apertured absorbent material 351 can be provided over the transmission layer 311. The first apertured absorbent layer 351 can include one or more apertures 329. In some embodiments, the apertures 329 can be sized and shaped to fit the electronics unit 350 therein. The first apertured absorbent layer 351 can be sized and shaped to the size of the electronics area and does not extend into the absorbent area. In some embodiments, the apertures 329 can be shaped and sized to fit the individual components of the electronics unit 350.

A second apertured absorbent layer 322 can be provided over the first absorbent layer 351. In some embodiments, the second absorbent layer 322 includes one or more apertures 328. The second absorbent layer 322 can be sized and shaped to the size of the electronics area and the absorbent area. In some embodiments, the apertures 328 can be shaped and sized to fit the individual components of the electronics unit 350.

An electronics unit 350 can be positioned in the apertures 328 and 329 of the first and second absorbent material 351 and 322. The electronics unit 350 can include a pump 327, power source 326, and a printed circuit board 381. In some embodiments, the pump 327 can include a pump inlet mechanism 710 and an outlet mechanism 382. In some embodiments, the printed circuit board 381 can include electronics including but not limited to a switch, sensors, and LEDs as described herein. In some embodiments, the circuit board 381 can include one or more hole to be positioned over one or more exhaust vents (not shown) in the outlet mechanism 382 as described in more detail herein.

An overlay layer 317 can be provided over the electronics components 350 and absorbent layer 322. In some embodiments, the overlay layer 317 can be one or more layers of absorbent and/or transmission material as described herein. In some embodiments, the overlay layer 317 can comprise a conformable material overlaying and overbordering the perimeter of the lower layers of transmission and absorbent materials. In some embodiments, the overlay layer 317 can soften the edges of the wound dressing layers by decreasing the profile around the edges of the dressing layers. The overlay layer 317 can protect the cover layer from being punctured by the lower layers when the cover layer is sealed over the dressing layers below. The overlay layer 317 can include an aperture 371 to allow access to at least a portion of the electronics unit 350 positioned below.

A cover layer or backing layer 313 can be positioned over the overlay layer 317. In some embodiments, when the overlay layer 317 is not used, the cover layer or backing layer 313 can be provided above absorbent layers 322, and/or electronic components 350. The cover layer 313 can form a seal to the wound contact layer 310 at a perimeter region enclosing the overlay layer 317, absorbent layers 322 and 351, electronic components 350, and the transmission layer 311. In some embodiments, the cover layer 313 can be a flexible sheet of material that forms and molds around the dressing components when they are applied to the wound. In other embodiments, the cover layer 313 can be a material that is preformed or premolded to fit around the dressing components as shown in FIG. 3A. As used herein, the terms cover layer and backing layer can be used interchangeably to refer to the layer of material in the dressing configured to cover the layers of the wound dressing.

In some embodiments, the cover layer or backing layer 313 can include an aperture 372. The aperture 372 can be positioned over at least a portion of the aperture 371 in the overlay layer 317 to allow access to at least a portion of the electronics unit 350 positioned below. In some embodiments, the apertures 371 and 372 can allow access to the switch and/or venting holes of the pump exhaust.

A label 341 can be provided over the apertures 371 and 372 and positioned over the exposed portion of the electronic components 350. The label can include the vent holes 342, indicator portions 344, and/or switch cover 343. The indicator portions 344 can include holes or transparent regions 344 for positioning over the one or more indicators or LEDs on the printed circuit board 381 below the label 341. The holes or transparent regions 344 can allow for the indicators or LEDs to be visible through the label 341. In some embodiments, the switch cover 342 can include a dome shaped cover positioned over the switch on the printed circuit board 381. In some embodiments, the label 341 can include embossed features for the switch cover 342. In some embodiments, the embossed features of the switch cover 342 can prevent accidental activation or deactivation of the device. In some embodiments, the switch or switch cover 342 can include a tab on the switch to prevent accidental activation or deactivation. The vent holes 342 of the label can allow exhaust from the pump outlet mechanism to pass through the label and exit the wound dressing to be exhausted to the atmosphere.

In some embodiments, the label can be positioned on top of the cover layer or backing layer 313. The label can seal to the cover layer to form a seal over the wound. In other embodiments, the label 341 can be positioned above the overlay layer 371 and below the cover layer or backing layer 313. In such embodiments, the cover layer 313 can have one or more apertures over one or more components of the label 341. For example, the cover layer 313 can have apertures over the vent holes 342, indicator portions 344, and/or switch cover 343.

Figure 3B:
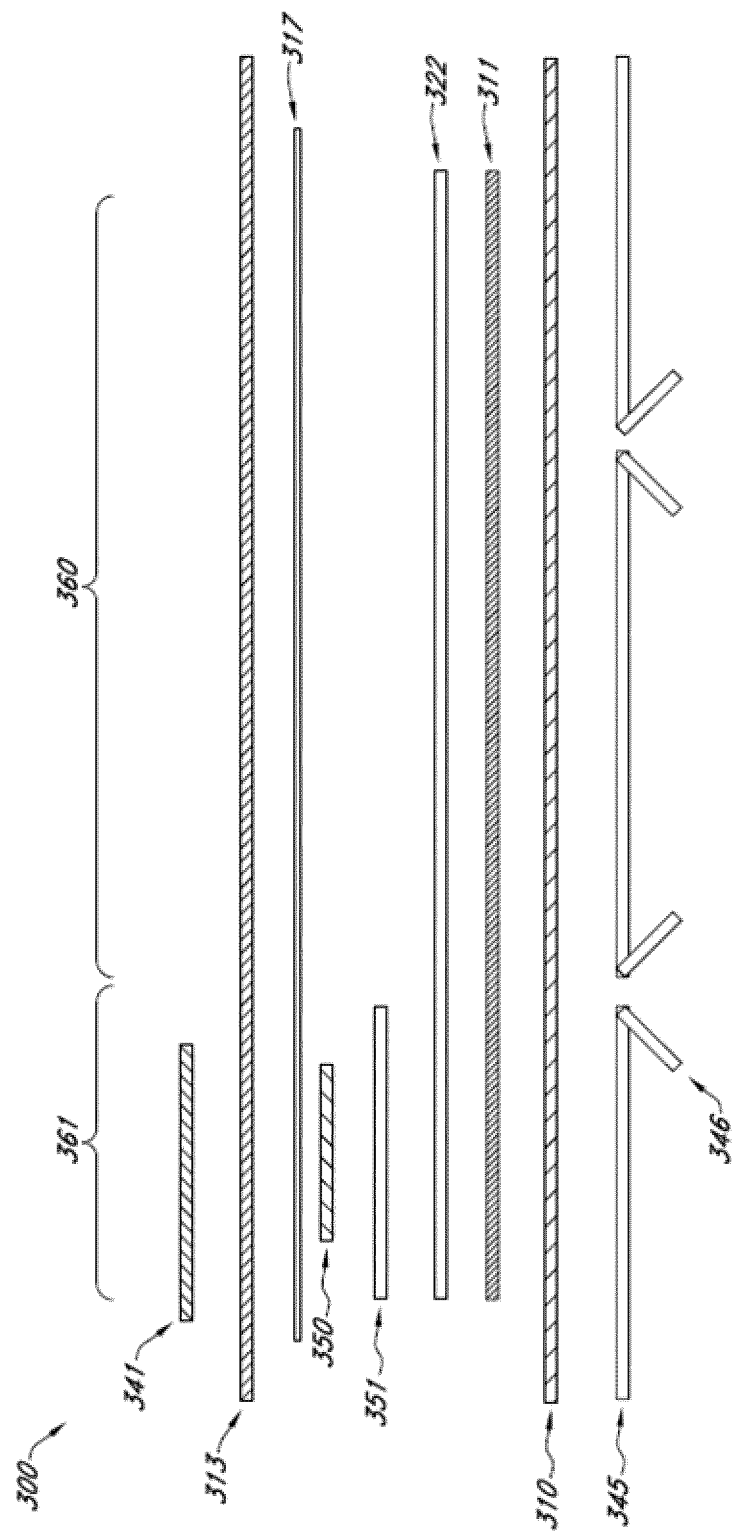
FIG. 3B illustrates a cross sectional layout of the material layers of the wound dressing incorporating an electronics assembly within the dressing.

FIG. 3B illustrates a cross sectional layout of the material layers of the wound dressing incorporating an electronics assembly within the dressing. The dressing 300 included multiple material layers and an electronics assembly 350. The wound dressing 300 can include an electronics area 361 including the electronics and an absorbent area or dressing area 360 that is intended to be applied to the wound as described with reference to FIGS. 1A-1C.

As described herein, the one or more material layers can extend into both the electronics area 361 and the dressing area 360. The dressing 300 can include a wound contact layer 310, transmission layer 311, absorbent layers 322 and 351, an overlay layer 317, and a cover or backing layer 313 as illustrated in FIG. 3B. The absorbent layers 322 and 351 can include recesses or cutouts to receive the components of the electronics assembly 350 as described herein. In some embodiments, as illustrated in FIG. 3B the small apertured absorbent layer 351 can be positioned on top of the large apertured absorbent layer 322. In other embodiments, as illustrated in FIG. 3A the small apertured absorbent layer 351 can be positioned on below of the large apertured absorbent layer 322.

In some embodiments, the overlay layer 317 and/or the cover layer 313 can include a cut out or aperture positioned over the switch and/or indicators of the electronics assembly 350. A label or covering 341 can be positioned to over at least a portion of the electronics assembly 350 and any cutouts in the overlay layer 317 and/or the cover layer 313. The label or covering 341 can be similar to the label or covering 341 as described previously with reference to FIG. 3A.

Before use, the dressing can include a delivery layer 345 adhered to the bottom surface of the wound contact layer. The delivery layer 345 can cover adhesive or apertures on the bottom surface of the wound contact layer 310. In some embodiments, the delivery layer 345 can provided support for the dressing and can assist in sterile and appropriate placement of the dressing over the wound and skin of the patient. The delivery layer 345 can include handles 346 that can be used by the user to separate the delivery layer 345 from the wound contact layer 310 before applying the dressing 300 to a wound and skin of a patient.

Figure 3C:
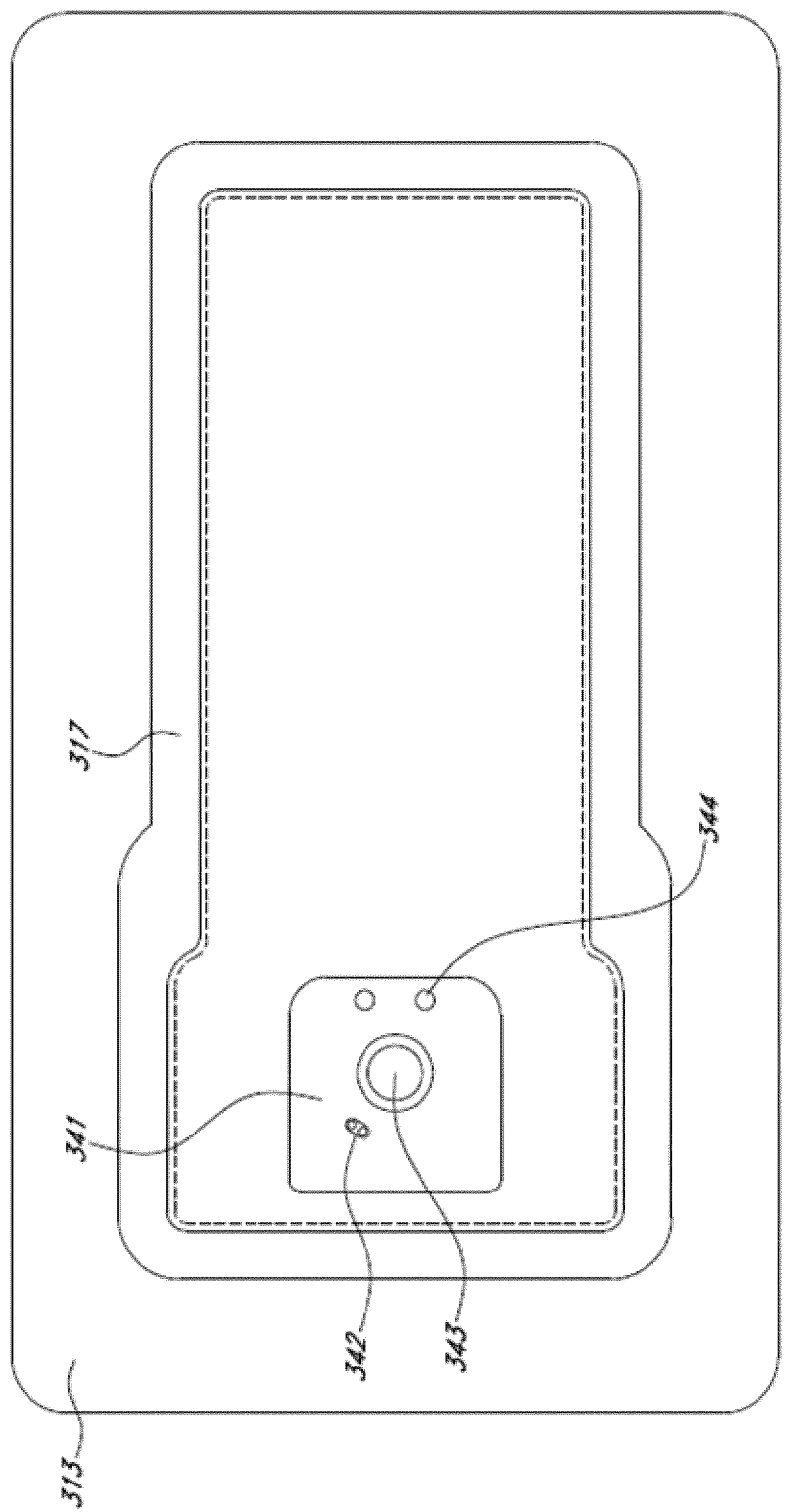
FIG. 3C illustrates a top view of an embodiment of the wound dressing incorporating an electronic assembly within the dressing.

FIG. 3C illustrates a top view of an embodiment of the wound dressing incorporating an electronic assembly within the dressing.

FIG. 3C shows a cover layer 313 and electronics covering 341 covering the overlay layer 317 and underlying dressing and electronics components. The cover layer 313 can seal to the wound contact layer 310 at a perimeter region of the wound contact layer 310. In some embodiments, the label or electronics covering 341 can be positioned over the cover layer 313. In other embodiments, the cover layer 313 can seal over the electronics covering 341. In some embodiments, the cover layer 313 can include one or more holes in the cover layer 313 positioned over the switch and/or pump outlet vent(s). In some embodiments, the cover layer 313 can include a single hole that is positioned over the switch cover 343, visual indicators 344, and/or pump outlet vent(s) 342 in the covering or label 341 as shown in FIG. 3C. In some embodiments, the label can include embossed features for the switch cover 343. In some embodiments, the embossed features of the switch cover 343 can prevent accidental activation or deactivation of the device. In some embodiments, the switch or switch cover 343 can include a tab on the switch to prevent accidental activation or deactivation.

The visual indicators 344 can provide an indication of operation of the negative pressure source and/or an indication of the level of negative pressure that is applied to the wound. In some embodiments, the visual indicators can include one or more light sources or LEDs. In some embodiments, the visual indicator light sources an illuminate to indicate a condition or change of condition. In some embodiments, the light source can illuminate in a particular sequence and/or color that indicates a condition. For example, in some embodiments, the light source can flash to notify the user that the device is operating properly. In some embodiments, the light source can automatically flash periodically and/or the light source can be activated by the switch or other button to light up and indicate a condition.

In some embodiments, the switch can be pressed and/or held down to power the dressing and electronics on and off. In some embodiments, once the switch is activated and the pump and associated colored LED, for example, green colored LED, can be used to conformed the dressing and integrated negative pressure source is operational. In some embodiments, during operation of the pump and dressing, the pump and dressing can enter the fault state indicated by a colored LED, for example, orange colored LED.

Reduced Pressure Therapy Systems and Methods

Figure 4:
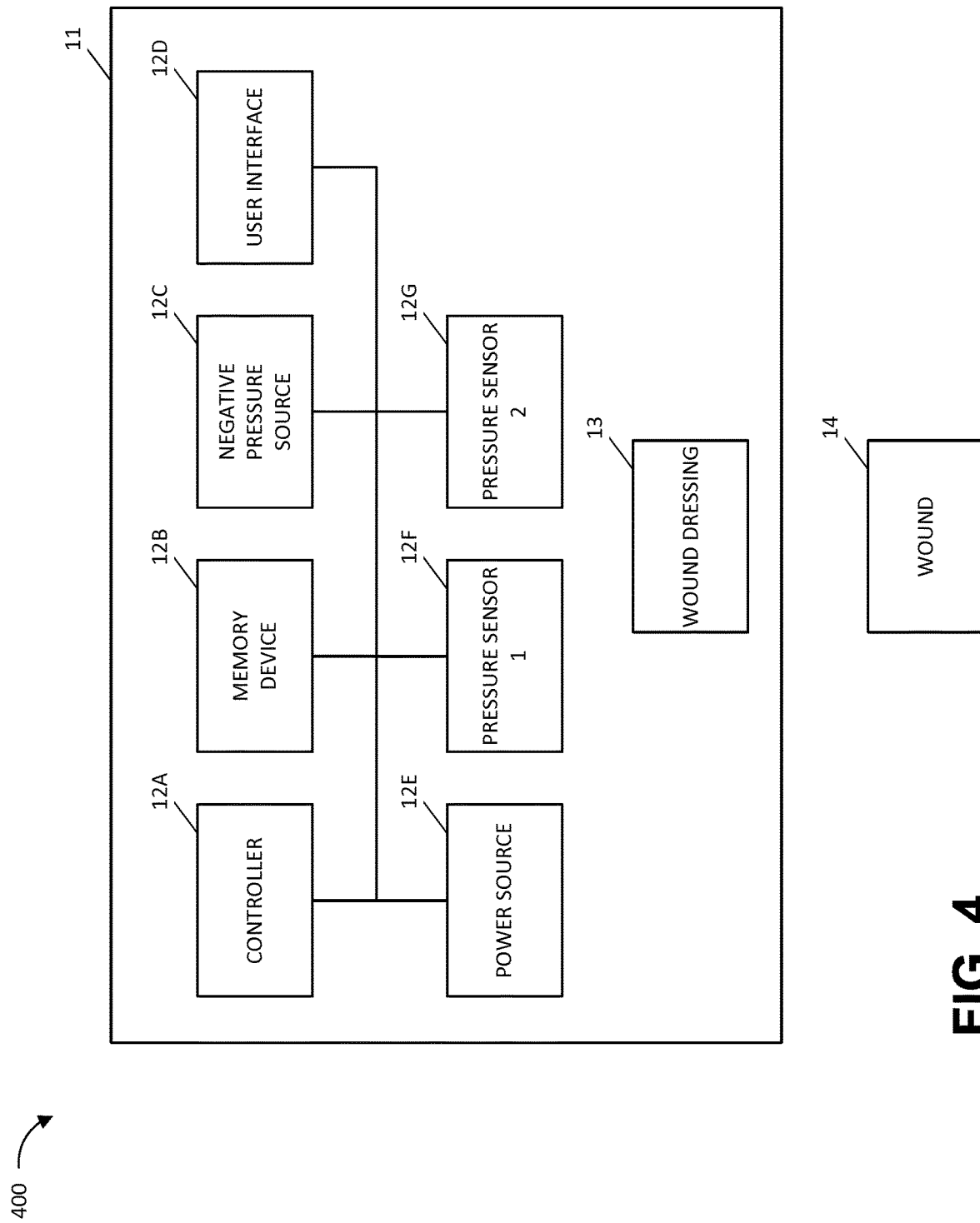
FIG. 4 illustrates a block diagram of various physical and electrical components of a negative pressure wound therapy system according to some embodiments.

FIG. 4 illustrates a negative pressure therapy system 100 that includes a TNP apparatus 11 applicable on a wound 14 according to some embodiments. The TNP apparatus 11 can be used to treat the wound 14. The TNP apparatus 11 can include controller 12A, memory 12B, a negative pressure source 12C, a user interface 12D, a power source 12E, a first pressure sensor 12F, and a second pressure sensor 12G that are configured to electrically communicate with one another. In addition, the TNP apparatus 11 can include a wound dressing 13. The power source 12E can provide power to one or more components of the TNP apparatus 11.

One or more of the controller 12A, memory device 12B, negative pressure source 12C, user interface 12D, power source 12E, first pressure sensor 12F, and second pressure sensor 12G can be integral with, incorporated as part of, attached to, or disposed in the wound dressing 13. The TNP apparatus 11 can accordingly be considered to have its control electronics and pump on-board the wound dressing 13 rather than separate from the wound dressing 13.

The controller 12A may be a microcontroller or microprocessor. The controller 12A can control the operations of one or more other components of the TNP apparatus 11 according at least to instructions stored in the memory device 12B. The controller 12A can, for instance, control operations of and supply of negative pressure by the negative pressure source 12C. The controller 12A can be a primary controller, and the TNP apparatus 11 can include one or more additional controllers as described herein.

The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a pump operated by a piezoelectric transducer, or any other suitable pump or micropump or any combinations of the foregoing. The pump can include an actuator driven by a source of energy, such as electrical energy, mechanical energy, and the like. For example, the actuator can be an electric motor, a piezoelectric transducer, a voice coil actuator, an electroactive polymer, a shape-memory alloy, a comb drive, a hydraulic motor, a pneumatic actuator, a screw jack, a servomechanism, a solenoid actuator, a stepper motor, a plunger, a combustion engine, and the like. In some embodiments, the negative pressure source 12C can supply negative pressure by converting electrical energy to mechanical energy without converting the electrical energy to magnetic energy. In such embodiments, the negative pressure source 12C can have a different impact when electrically coupled to one or more other components of the controller 12A than if the negative pressure source 12C supplied negative pressure by converting the electrical energy to the magnetic energy and then to the mechanical energy.

The user interface 12D can include one or more elements that receive user inputs or provide user outputs to a patient or caregiver. The one or more elements that receive user inputs can include buttons, switches, dials, touch screens, or the like, and the one or more elements that provide user outputs can include activation of a light emitting diode (LED) or one or more pixels of the display or activation of a speaker or the like. In one example, the user interface 12D can include a switch to receive user inputs (for instance, a negative pressure activation or deactivation input) and two LEDs to indicate an operating status (for example, functioning normally, under fault condition, or awaiting user input) of the TNP apparatus 11. The user interface 12D may also include input elements that change the state of the controller 12A by employing switching mechanisms, such as a pull tab (further described with respect to FIG. 8A and 8B).

The first pressure sensor 12F can be used to monitor pressure underneath the wound dressing 13, such as pressure in a fluid flow path connecting the negative pressure source 12C and the wound 14, pressure at the wound 14, or pressure in the negative pressure source 12C. The second pressure sensor 12G can be used to monitor pressure external to the wound dressing 13. The pressure external to the wound dressing can be atmospheric pressure; however, the atmospheric pressure can vary depending on, for instance, an altitude of use or pressurized environment in which the TNP apparatus 11 may be used.

The controller 12A can control the supply of negative pressure by the negative pressure source 12C according at least to a comparison between the pressure monitored by the first pressure sensor 12F and the pressure monitored by the second pressure sensor 12G.

The wound dressing 13 can include a wound contact layer, a spacer layer, and an absorbent layer. The wound contact layer can be in contact with the wound 14. The wound contact layer can include an adhesive on the patient facing side for securing the dressing to the skin surrounding the wound 14 or on the top side for securing the wound contact layer to a cover layer or other layer of the wound dressing 13. In operation, the wound contact layer can provide unidirectional flow so as to facilitate removal of exudate from the wound while blocking or substantially preventing exudate from returning to the wound 14. The spacer layer can assist in distributing negative pressure over the wound site and facilitating transport of wound exudate and fluids into the wound dressing 13. Further, the absorbent layer can absorb and retain exudate aspirated from the wound 14.

The controller 12A can monitor the activity of the negative pressure source 12C, which may include monitoring a duty cycle of the negative pressure source 12C (for example, the duty cycle of the actuator of the negative pressure source). As is used herein, the "duty cycle" can reflect the amount of time the negative pressure source 12C is active or running over a period of time. In other words, the duty cycle can reflect time that the negative pressure source 12C is in an active state as a fraction of total time under consideration. Duty cycle measurements can reflect a level of activity of the negative pressure source 12C. For example, the duty cycle can indicate that the negative pressure source 12C is operating normally, working hard, working extremely hard, etc. Moreover, the duty cycle measurements, such as periodic duty cycle measurements, can reflect various operating conditions, such as presence or severity of leaks, rate of flow of fluid (for instance, air, liquid, or solid exudate, etc.) aspirated from a wound, or the like. Based on the duty cycle measurements, such as by comparing the measured duty cycle with a set of thresholds (for instance, determined in calibration), the controller can execute or be programmed to execute algorithms or logic that control the operation of the system. For example, duty cycle measurements can indicate presence of a high leak, and the controller 12A can be programmed to indicate this condition to a user (for instance, patient, caregiver, or physician) or temporarily suspend or pause operation of the source of negative pressure in order to conserve power.

When the TNP apparatus 11 may be used to treat the wound 14, the wound dressing 13 can create a substantially sealed or closed space around the wound 13 and under the wound dressing 13, and the first pressure sensor 12F can periodically or continuously measure or monitor a level of pressure in this space. The controller 12A can control the level of pressure in the space between a first negative pressure set point limit and at least a second negative pressure set point limit. In some instances, the first set point limit can be approximately −70 mmHg, or from approximately −60 mmHg or less to approximately −80 mmHg or more. In some instances, the second set point limit can be approximately −90 mmHg, or from approximately −80 mmHg or less to approximately −100 mmHg or more. The controller 12A may operate the negative pressure source 12C such that a lower pressure is maintained at the first pressure sensor 12F than at outside atmosphere at the second pressure sensor 12G.

Sterilization of the TNP apparatus

As described, TNP systems come in various sizes, from small to large. Also, as described here, such as in connection with FIGS. 1A-3C, some TNP systems have electronics and power source integrated in the dressing. These integrated systems can advantageously have quieter and easier application or operation, increased portability, reduced maintenance efforts, simpler aesthetics, or the like. However, although integrated TNP systems carry these and other numerous advantages, safe production and operation of the systems may pose a unique challenge when it comes to sterilization of the system.

Because TNP systems are applied on wounds, it is important that the systems and its components are free from bacteria. A risk of bacterial infection may undermine the wound healing purpose of the TNP systems. For non-integrated TNP systems in which pump and pump electronics positioned remotely from the dressing, sterilization is simpler matter as the dressing may be sterilized separately from the pump and pump electronics. The dressing, pump, and pump electronics can be sterilized with low temperature sterilization techniques such as passing an antibacterial gas through the dressing. In some embodiments, ethylene oxide (EtO) can be used for sterilization as it is a colorless gas that effectively attacks the cellular proteins and nucleic acids of microorganisms. The sterilized dressing may be applied on or near to wounds, the negative pressure pumps may later be connected to the dressing, and the activated for operation.

However, in some cases, sterilization of the integrated negative pressure wound therapy systems is not a simple matter. Because the power source, the electronics, and negative pressure source can be positioned in or on the dressing, using same or similar sterilization techniques as for non-integrated TNP systems may expose other components to the sterilizing gas. This exposure can be problematic because EtO is flammable.

In some implementations, non-integrated devices can be powered using replaceable batteries. During sterilization, the batteries can be disconnected from the electronics such that the electronics are unpowered and therefore cannot have stored energy that may present a hazard for igniting EtO during sterilization.

In some embodiments, integrated systems include a non-removable power source that is positioned in or on the wound dressing. This presents a risk of inadvertent activation of the TNP system during sterilization, which may lead to some of the electrical energy from the power source being stored in one or more energy storing components of the TNP system electronics, such as capacitors. Release of such stored energy can cause overrating, creating a spark, and/or ignite sterilization gas during sterilization. Accordingly, the risk of a sudden energy release during the sterilization process should be addressed.

In some embodiments, the power source can be isolated from the rest of electronics in integrated TNP systems such that unwanted release of energy is avoided. This can be accomplished through isolating the power source from the electronics during sterilization and including two (or more) activation circuits configured to, respectively, couple a decoupled power source to the electronics and activate operation of the TNP system. Certain implementations refer to such arrangements as two-step activation.

Two-Step Activation

Figure 5:
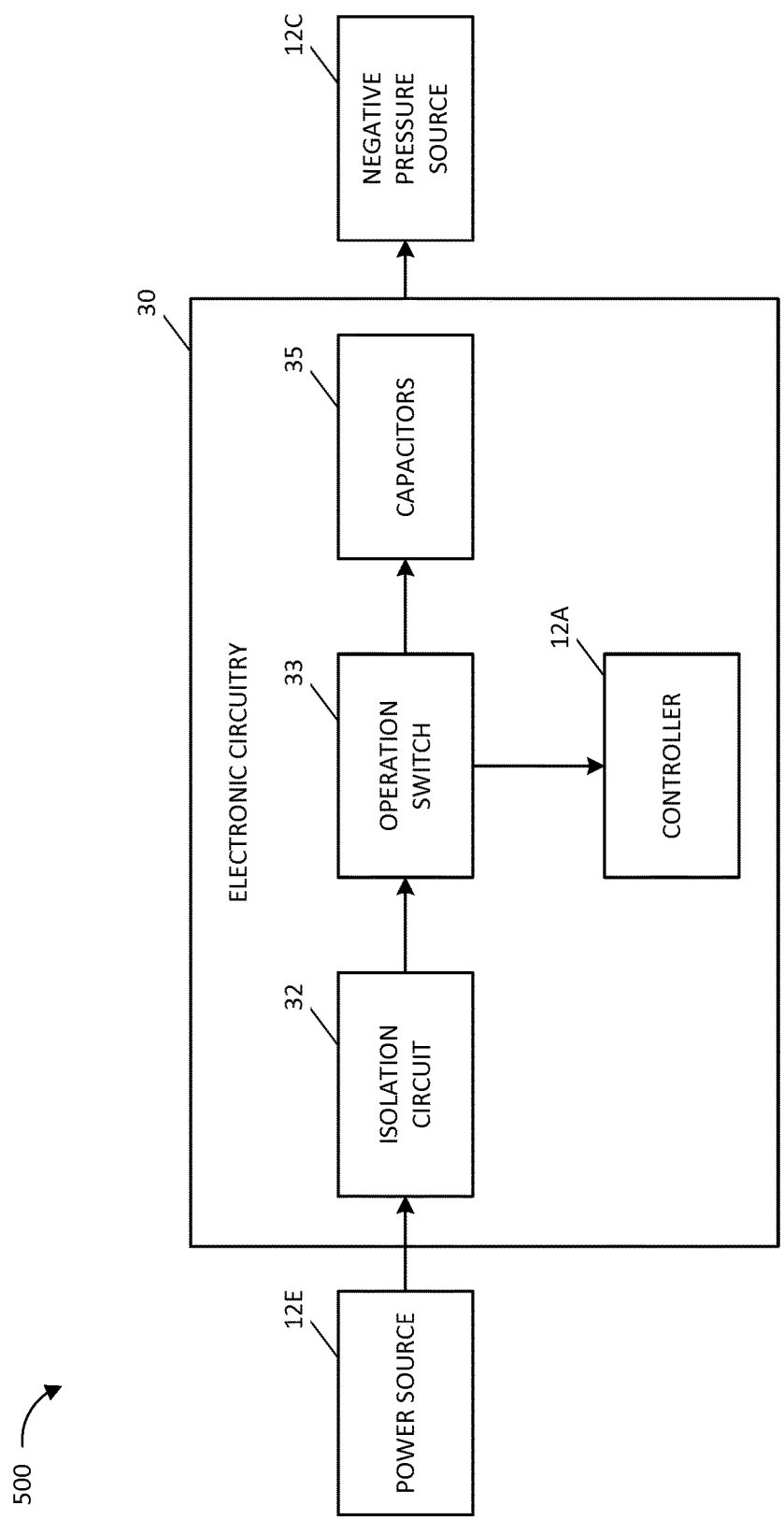
FIG. 5 illustrates a block diagram of a negative pressure wound therapy system configured to isolate an electronic circuitry from a power source according to some embodiments.

FIG. 5 illustrates a block diagram 500 of a TNP system configured to isolate an electronic circuitry from a power source according to some embodiments. The system 500 includes the power source 12E, electronic circuitry 30, and the negative pressure source 12C. The electronic circuitry 30 includes the controller 12A, an isolation circuit 32, an operation switch 33, and one or more capacitors 35. As described herein, activation of the operation switch 33 can activate the controller 12A and activate charging of the one or more capacitors 35, which will store energy and can supply energy (for example, current) to the negative pressure source 12C. FIG. 5 illustrates how the isolation circuit 32 can prevent the power source 12E from electrically coupling with the rest of the electronic circuitry 30 according to some embodiments.

The power source 12E can include one or more power supplies, such as batteries (which may be boosted, AC and/or DC) to provide power for one or more components of the TNP apparatus, such as the TNP apparatus 11, including the electronic circuitry 30 and the negative pressure source 12C. The power source 12E can, for instance, provide electrical current and voltage to the isolation circuit 32. The voltage output by the power source 12E can include one or more of around 3 V, 6 V, 27 V, or the like in some implementations. The power source 12E and/or electronic circuitry 30 can additionally include circuitry, such as a boost converter, to control the provided electrical current and voltage. In some implementations, a power conversion is performed between the one or more capacitors 35 and the negative pressure source 12C. For example, the boost converter can increase the output of the power source 12E to charge the one or more capacitors 35 and/or power the negative pressure source. In some cases, the boost converter may not boost the output of the power source, but instead control a therapy device and/or control one or more sensors of the system. In such cases, the boost converter can operate as a secondary power controller (in addition to the primary controller). The secondary power controller can turn on/off the source of negative pressure and/or another therapy device, such as an ultrasound generator, oxygen concentrator, cold plasma generator, or the like.

The isolation circuit 32 can isolate the power source 12E from electrically coupling with the rest of the electronic circuitry 30. In some embodiments, the isolation circuit 32 operates in two or more states. In the first "off" state, the isolation circuit 32 operates as an open circuit, which prevents the output of the power source 12E to be supplied to the other components of the electronic circuitry 30. In this state, the one or more capacitors 35 cannot store any charge, which prevents accidental overheating, sparking, and/or igniting EtO during sterilization even if the operation switch 33 is inadvertently activated. In the second "on" state, the isolation circuit 32 allows the output of the power source 12E to be supplied to the other components of the electronic circuitry 30, which can result in the one or more capacitors 35 storing electrical energy.

When the isolation circuit 32 is in the first "off" state, the isolation circuit 32 does not provide the negative pressure source 12C with power from the power source 12E. On the other hand, when the isolation circuit 32 is in the second "on" state, depending on the state of the operation switch 33, operation power may be provided to the negative pressure source 12C for provision of negative pressure wound therapy.

As is illustrated in FIG. 5, the operation switch 33 is electrically connected to the power source 12E and the negative pressure source 12C and is located between the two. The operation switch 33 may operate in two or more states. In first "off" state, the operation switch 33 prevents operation of the negative pressure source 12C. In second "on" state, the operation switch 33 allows the operation of the negative pressure source 12C. In some cases, the operation switch 33 may be located closer to or further from the power source 12E than the isolation circuit 32.

In some embodiments, switching the state of isolation circuit 32 to the "on" state (such as, activating the isolation circuit 32) may represent step 1 of activation. Switching the state of operation switch 33 to the "on" state (such as, activating the operation switch 33), may represent step 2 of activation. Together, the steps may form two-step activation that provides safe sterilization of integrated TNP systems. Regarding step 1, when the isolation circuit 32 is in the first "off" state, because no power is received or seen by the rest of the components of the electronic circuitry 30, activating the operation switch 33 would not power one or more of the other components. On the other hand, when the isolation circuit 32 is in the second "on" state, each state of the operation switch 33 activates (operation switch 33 "on") or deactivates (operation switch 33 "off") the operation of one or more of the controller 12A, one or more capacitors 35, or the negative pressure source 12C. One skilled in the art would recognize various alternative circuit configurations that can carry out the two-step activation as described in some implementations. For example, in some cases, the controller 12A can receive power from the power source 12E regardless of the state of the isolation circuit. The controller 12A can operate in a low power mode until the isolation circuit 32 transitions to the "on" state. When the isolation circuit 32 is on the "off" state, power may not be provided to the boost converter as described herein.

In some implementations, the controller 12A controls operation of the negative pressure source 12C by outputting one or more control signals to one or more inputs of a driving circuit (not shown), which is electrically coupled with the negative pressure source 12C. In some embodiments, the controller 12A can vary a pulse width modulation (PWM) of output control signals to adjust an electrical current or voltage provided by the driving circuit to the negative pressure source 12C.

Although the one or more capacitors 35 are illustrated as example components that can store electrical energy, it should be understood that the capacitors are not the only type of component that can store electrical energy. Depending on possible circuit variations embodying the ideas in this present disclosure, other energy storing components may be alternatively or additionally used. In some cases, the one or more capacitors 35 may be placed to shunt away and conceal current fluctuations, provide power factor correction, provide AC coupling or decoupling, suppress noise and spikes, tune circuits, and/or any other purpose capacitors are used in a circuit.

Figure 6A:
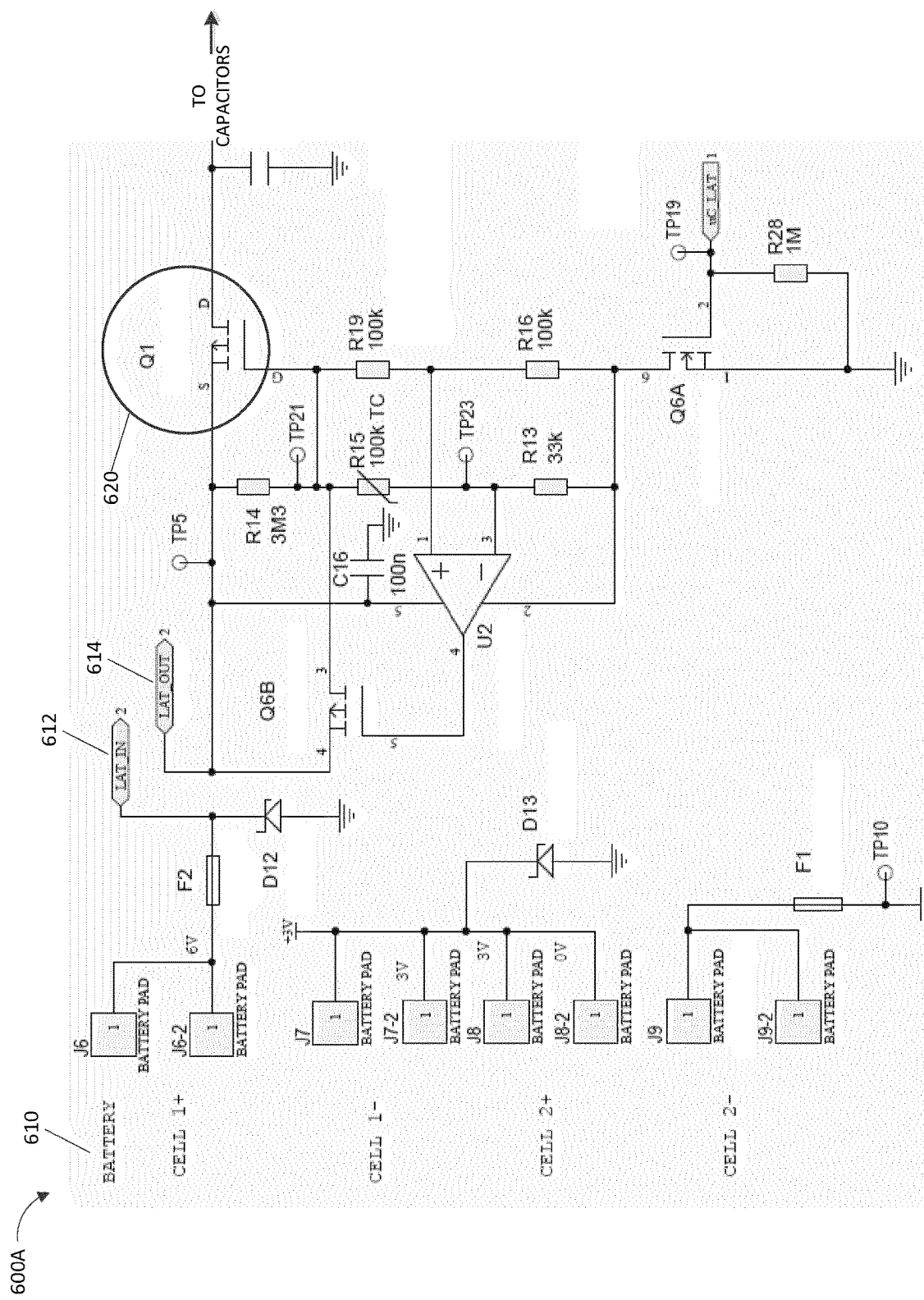
FIGS. 6A and 6B illustrate circuit diagrams of electronic circuitry of a negative pressure wound therapy system according to some embodiments.
Figure 6B:
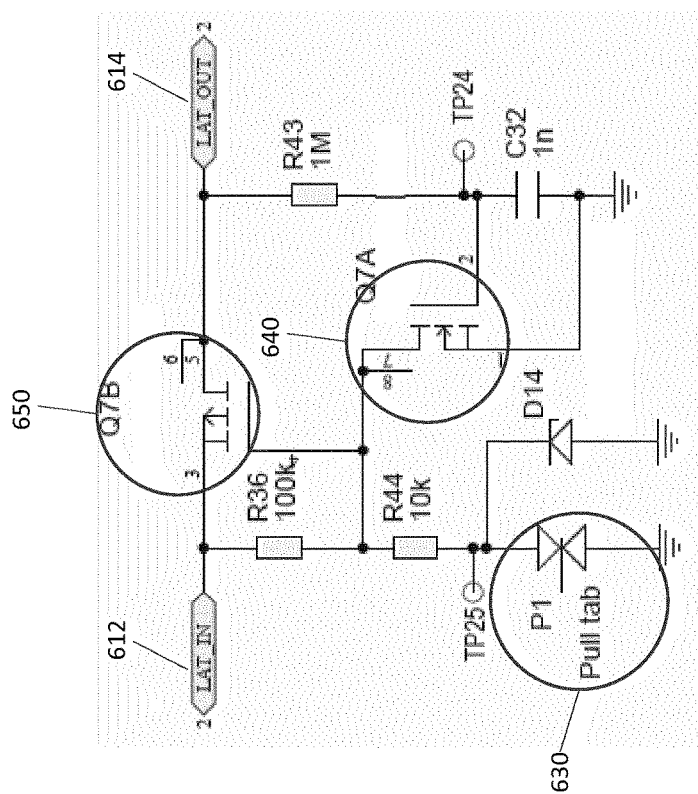

FIGS. 6A and 6B illustrate circuit diagrams of electronic circuitry of a negative pressure wound therapy system according to some embodiments. Referring to FIG. 6A, a circuit 600A includes a power source 610 and terminals or pins LAT_IN 612 (representing "latching circuit pin in") and LAT_OUT 614 (representing "latching circuit pin out") for connecting an isolation circuit 600B as illustrated in FIG. 6B (which can be the same or similar to the isolation circuit 32 of FIG. 5). The power source 610 (illustrated as two batteries CELL 1 and CELL 2) is connected to pin 612.

In some embodiments, when the isolation circuit 600B is in the "on" state (or activated), current flows between the pins 612 and 614. In turn, if an operation switch (not illustrated) is activated (or in the "on" state), switch 620 (illustrated as a transistor) is turned on, which allows the one or more capacitors (not shown) to be charged from the power source 610. If the isolation circuit 600B is in the "off" state (or deactivated), current does not flow between the pins 612 and 614. Regardless of the state of the operation switch, switch 620 will not be turned on and the one or more capacitors will not be charged when the isolation circuit 600B is deactivated. As described herein, this operation reduces the risk of energy stored by, for example, one or more capacitors, overheating, creating a spark, and/or igniting sterilization gas during sterilization of the whole integrated TNP systems.

FIG. 6B provides an isolation circuit 600B according to some embodiments. The circuit 600B can be connected between the pins LAT IN 612 and LAT OUT 614 of FIG. 6A. The circuit 600B includes an activation switch or another mechanism 630, such as a pull tab, for activating the circuit. When the activation switch 630 is not activated (such as, the pull tab not pulled), switches 640 and 650 are closed or off such that no current flows between the pins 612 and 614. When the activation switch 630 is activated (for example, pulled as described herein), an electrical path is provided (for example, to ground) permitting current to flow. This can activate switch 650, which allows current to flow between the pins 612 and 614. As is illustrated, switch 650 can be PFET transistor (for example, PMOS transistor) activated (such as, becoming electrically conductive) when current flows from the pin 612 (connected to the power source 610 as illustrated in FIG. 6A) through the electrical path provided by the activated activation switch 630. The current can activate the switch 650 (for example, PFET transistor), and the switch 650 can provide an electrical path between pins 612 and 614 for the current. Activation of switch 650 in turn can cause switch 640, which can be NFET transistor (for example, NMOS transistor) as is illustrated, to be activated (such as, become electrically conductive). Once switch 650 is activated, current can flow between the pins 612 and 614, thereby allowing switch 620 to be turned on as described herein. In some cases, when the isolation circuit 600B transitions to the on state, power is provided to the boost converter. For example, this can result in charging of one or more energy storing components, such as one or more capacitors, that can power the source of negative pressure.

In some embodiments, isolation circuit 600B is a self-latching circuit. The circuit 600B can operate so that once the activation switch 630 has been activated, the circuit 600B remains activated allowing current to flow between the pins 612 and 614 even if the activation switch 630 is subsequently deactivated. In such cases, once switches 650 and 640 are activated and power continues to be applied to the pin 612, the circuit 600B is not configured to be reset so that the circuit will continue to operate in the "on" state. Power may be continuously applied to the pin 612 by a permanently connected battery or another power source. In some cases, latching is provided by activating the switch 640 as described herein. Once initially activated, the switch 640 (for example, NFET transistor) can remain activated regardless of the state of the activation switch 630. The switch 640 can provide an electrical path for the current (for example, to ground) necessary to maintain the switch 650 activated even if the activation switch 630 is deactivated and no longer provides an electrical path for the current. For example, the switch 640 can remain activated because source of the NFET transistor is connected to the ground, which maintains the transistor in active state when voltage is applied to the gate from the pin 612.

In certain implementations, once isolation circuit 600B provides electric connection between pins 612 and 614, a user of the TNP system may activate an operation switch (such as switch 32 of FIG. 5) to cause the controller 12A to wake up and turn switch 620 on, which will allow one or more capacitors (such as the one or more capacitors 35 of FIG. 5) to be charged. A person skilled in the art would readily understand that a choice of PMOS and NMOS transistor switches and other circuit elements may have some variances. Also, as described herein, pull tab 630 may be replaced by other activation mechanisms, such as one or more buttons. In some cases, the activation mechanism 630 can be a power source, such as a secondary power source that can be additional to the power source described herein (which can serve as a primary power source). In some cases, the secondary power source can have a larger capacity than the primary power source. Connecting or plugging in the secondary power source can present a greater risk of overheating, creating a spark, and/or igniting sterilization gas during sterilization of the TNP apparatus.

In some cases, the state of the isolation circuit 600B can be communicated to the user using one or more indicators (for example, the one or more indicators 266). For example, inactive state of the isolation circuit can be indicated to the user. This can prompt the user attempting to start provision of negative pressure wound therapy to activate the isolation circuit, for instance, by pulling the pull tab, pressing a button, activating a switch, connecting or plugging in the secondary power source, or the like. As another example, active state of the isolation circuit can be indicated to the user. This can indicate to the user that the activation was successful.

Figure 7:
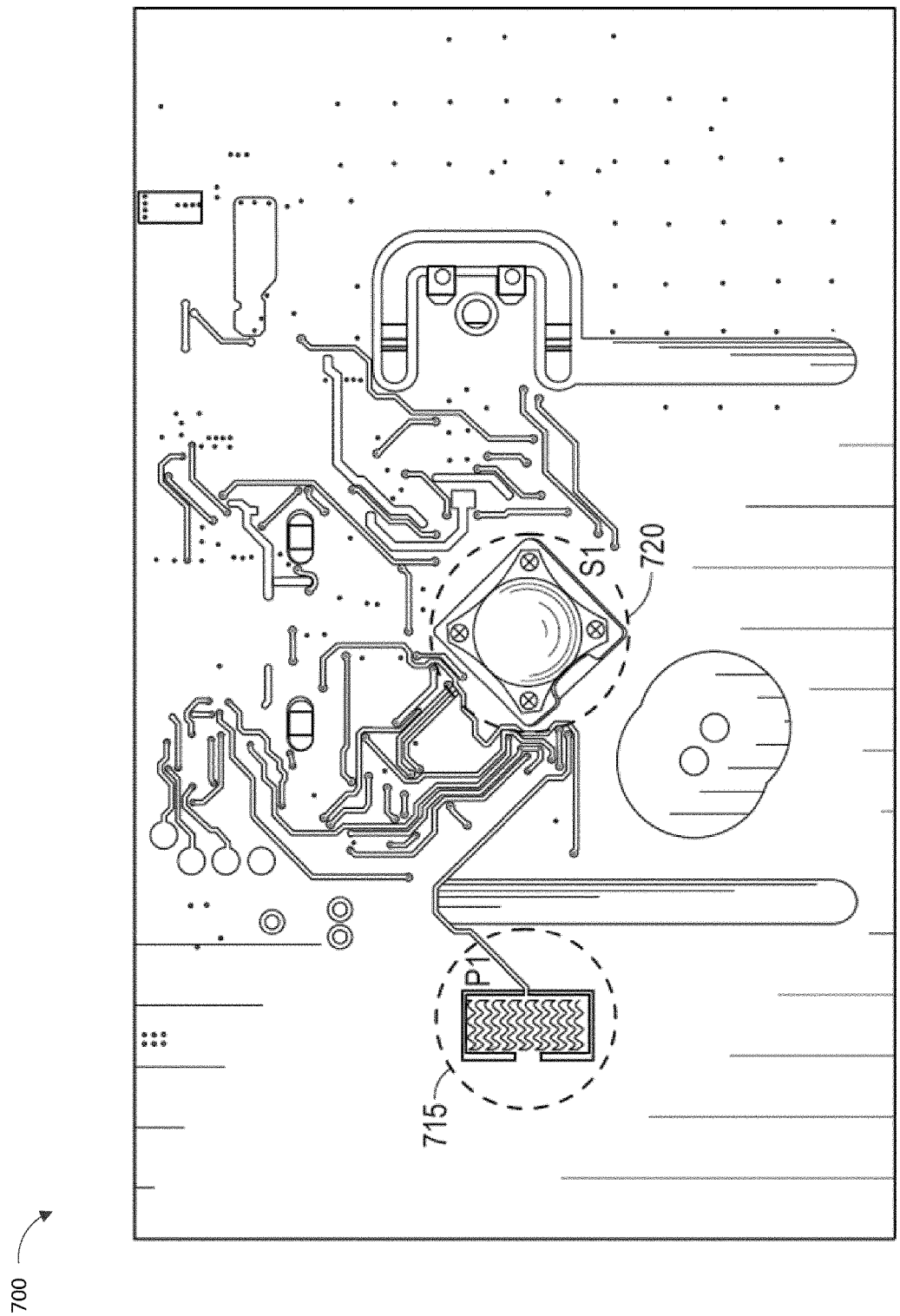
FIG. 7 illustrates a back view of a printed circuit board (PCB) configured to perform two-step activation according to some embodiments.

FIG. 7 illustrates a back view of a printed circuit board (PCB) 700 configured to perform two-step activation according to some embodiments. The PCB 700 includes an activation switch 715, which can be operated by a pull tab, and an operation switch 720. Switch 715 includes conductive "fingers" or paths, which are not electrically connected when an isolation circuit is in the "off" state. A pull tab 810 (FIG. 8A) may be attached on the opposite side of the PCB 700, and when pulled out, cause the two sets of the fingers come in electrical contact with each other, which cases the isolation circuit to be in the "on" state. For example, fingers can be squeezed toward each other, electrically connected as explained in connection with FIG. 9C, or the like. The multitude of fingers of the switch 715 can ensure that electrical connection is made when the pull tab 810 is pulled out. This type of structure may be used with step 1 activation (for example, activation of the isolation circuit 32 of FIG. 5) after sterilization has been completed. FIG. 7 illustrates the switch 715 that cannot be deactivated after activation as the conductive fingers remain in electrical contact after the pull tab 810 has been pulled by a user.

It should be noted that while the illustrated switch 715 is configured for an irreversible activation (for example, it is not easy to de-compress the fingers such that they are no longer electrically connected), reversible activation mechanisms may also be used as described herein. Additionally, other types of activation/switching mechanisms may be used based on various engineering or aesthetic considerations.

The PCB 700 also illustrates a backside of the operation switch 720 (described as 33 in FIG. 33) configured for step 2 activation. Its frontside can be a dome-type switch 820 as shown in FIG. 8B. Pressing the dome switch activates or deactivates step 2 of the two-step activation.

Figure 8A:
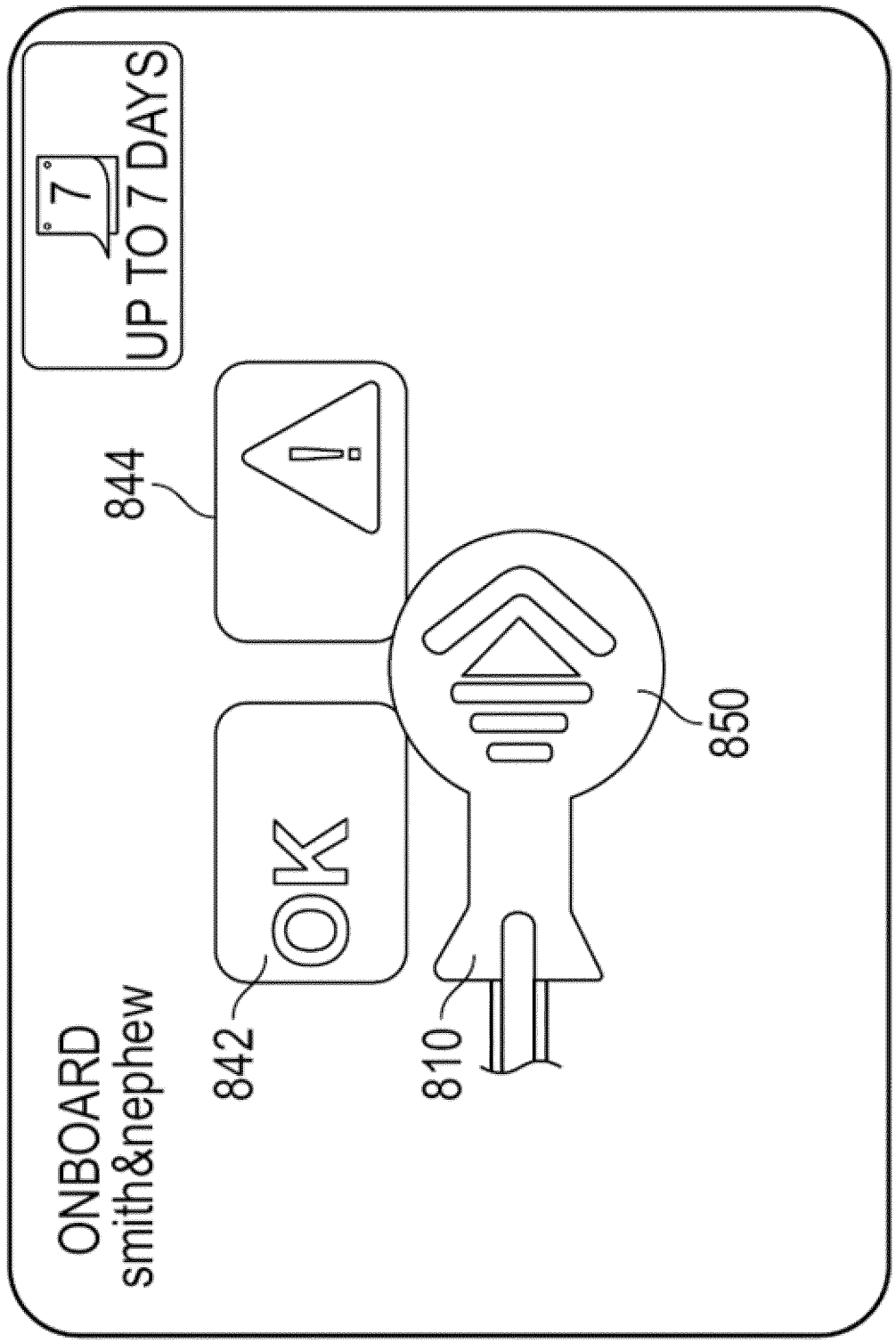
FIGS. 8A and 8B illustrate front view of the two-step activation PCB with a pull tab before and after a pullout, respectively, according to some embodiments.
Figure 8B:
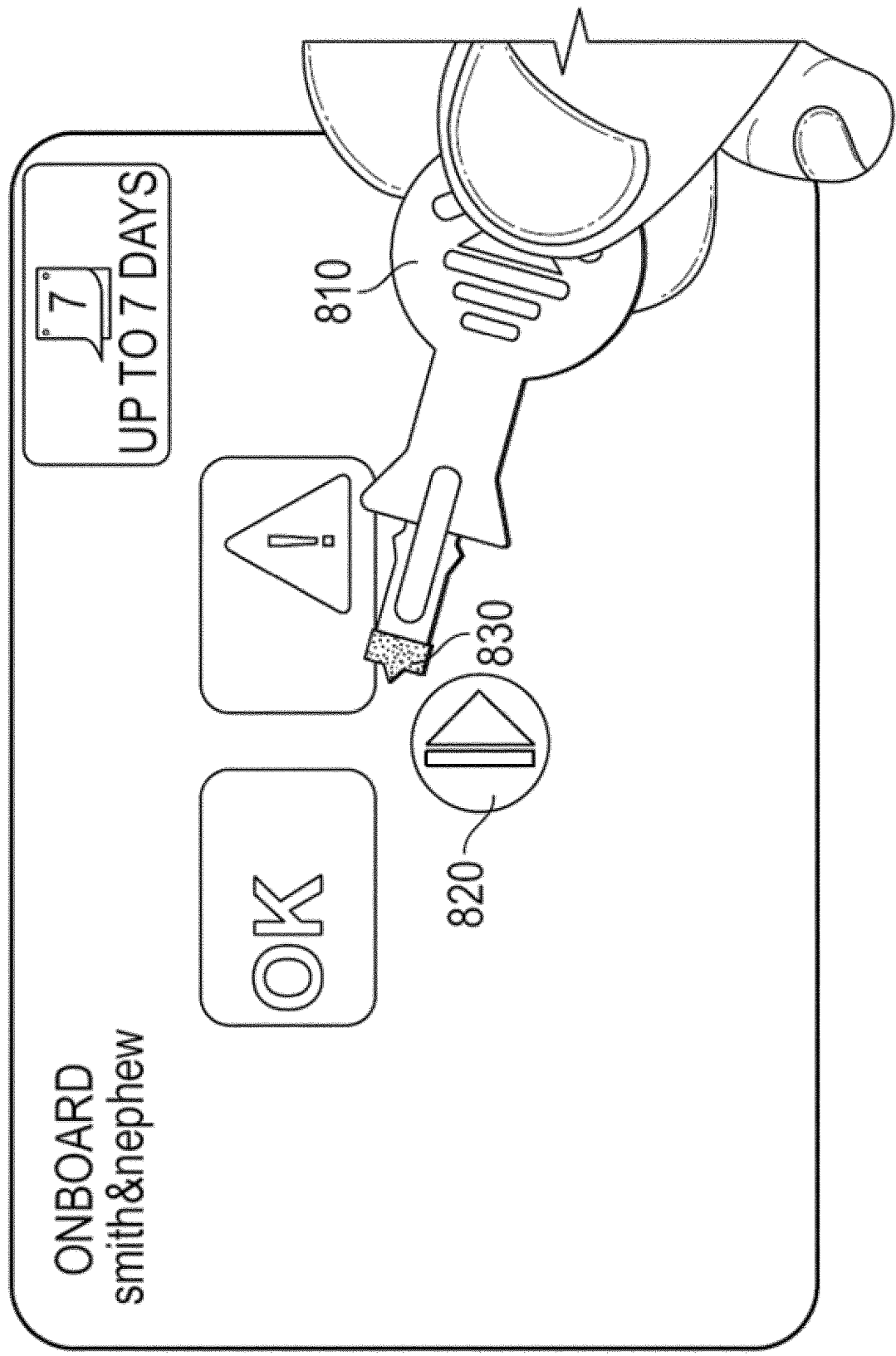

FIGS. 8A and 8B illustrate front view of the two-step activation PCB with a pull tab before and after a pullout, respectively, according to some embodiments. In the illustrated embodiment, the pull tab 810 is removed to reveal the dome-type switch 820, thereby reducing the likelihood that the two-step activation may be executed in a reverse order. As is illustrated in FIG. 8B, removal of the pull tab 810 causes removal of isolating material 830 from the surface of the switch 715 (FIG. 7) so that electrical connection is formed between the fingers of the switch. Also illustrated are indicators 842 and 844 that can indicate the state of operation of the TNP apparatus. The pull tab 810 includes a pattern 850 instructing the user to pull the tab in a particular direction (for example, to the left in the illustrated embodiment).

Figure 9A:
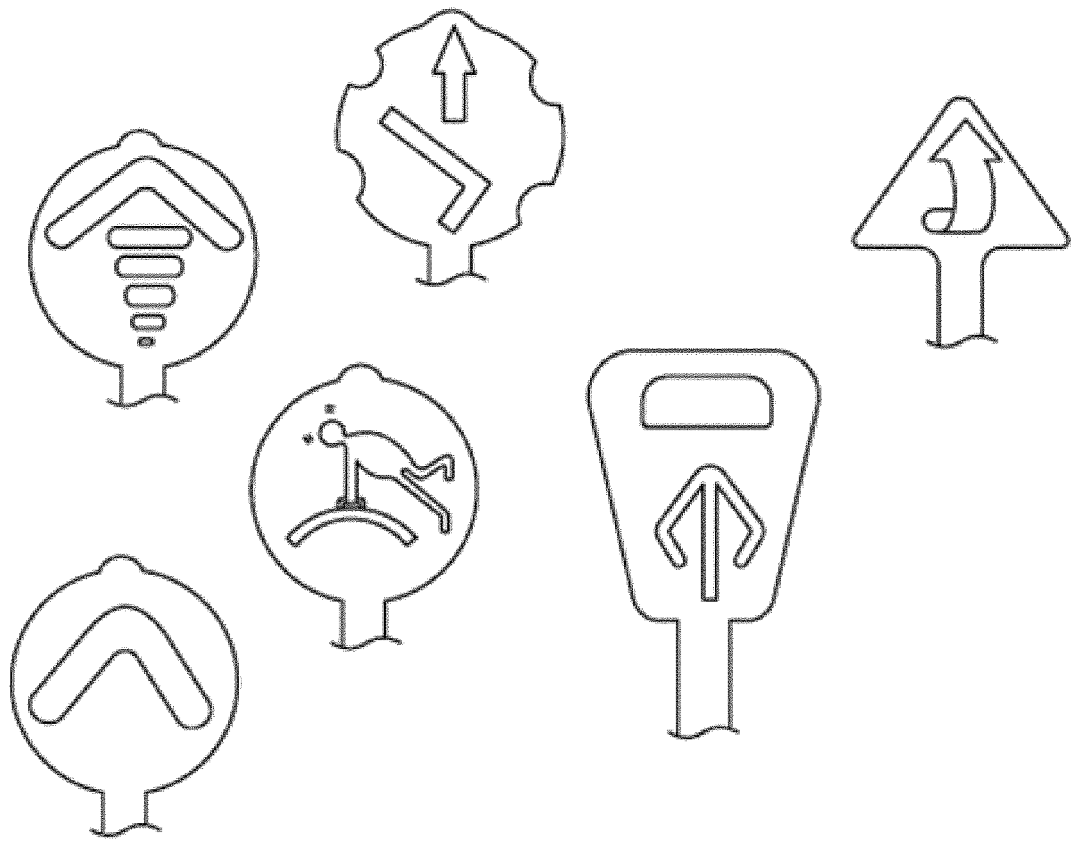
FIGS. 9A-9C illustrate various designs for the pull tab according to some embodiments.
Figure 9B:
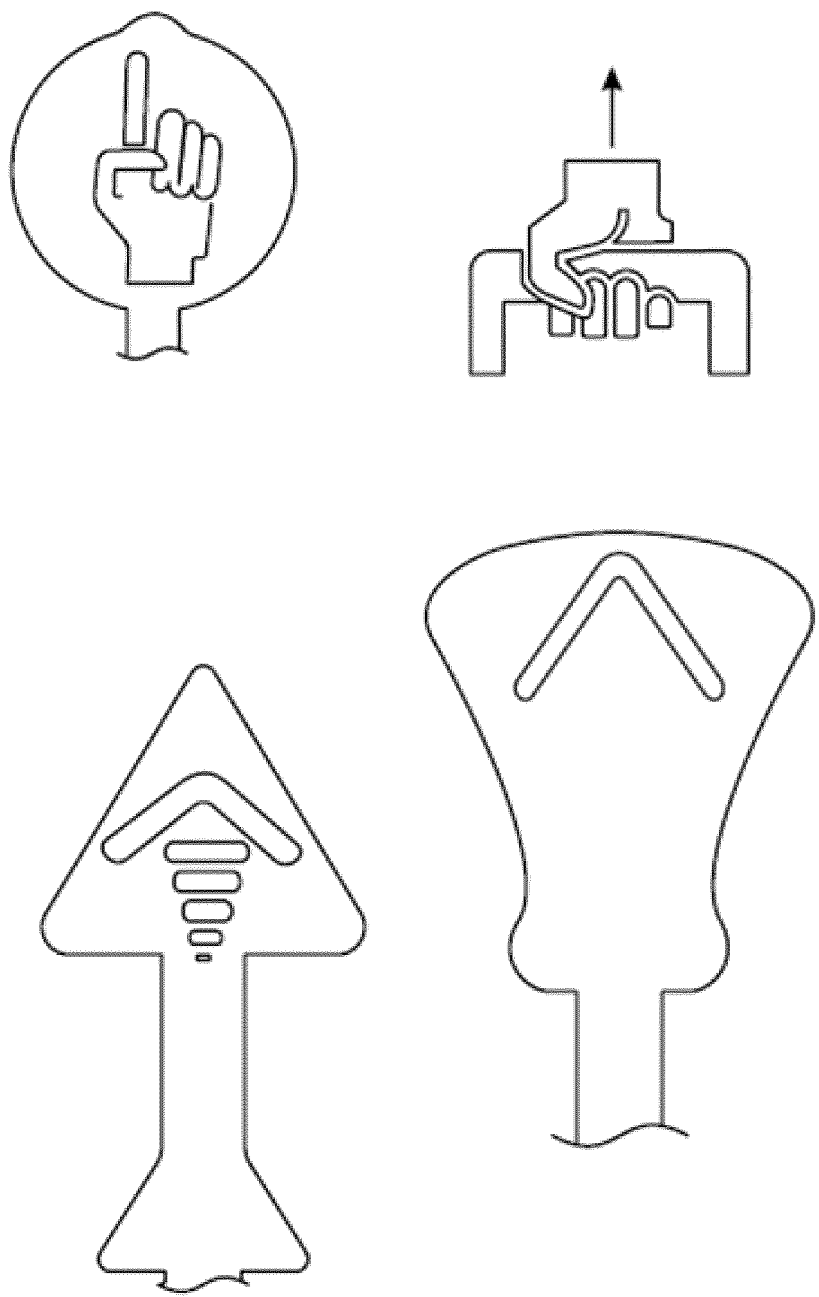

FIGS. 9A and 9B illustrate various designs of the shapes and patterns of the pull tab, such as the pull tab 810, according to some embodiments.

Figure 9C:
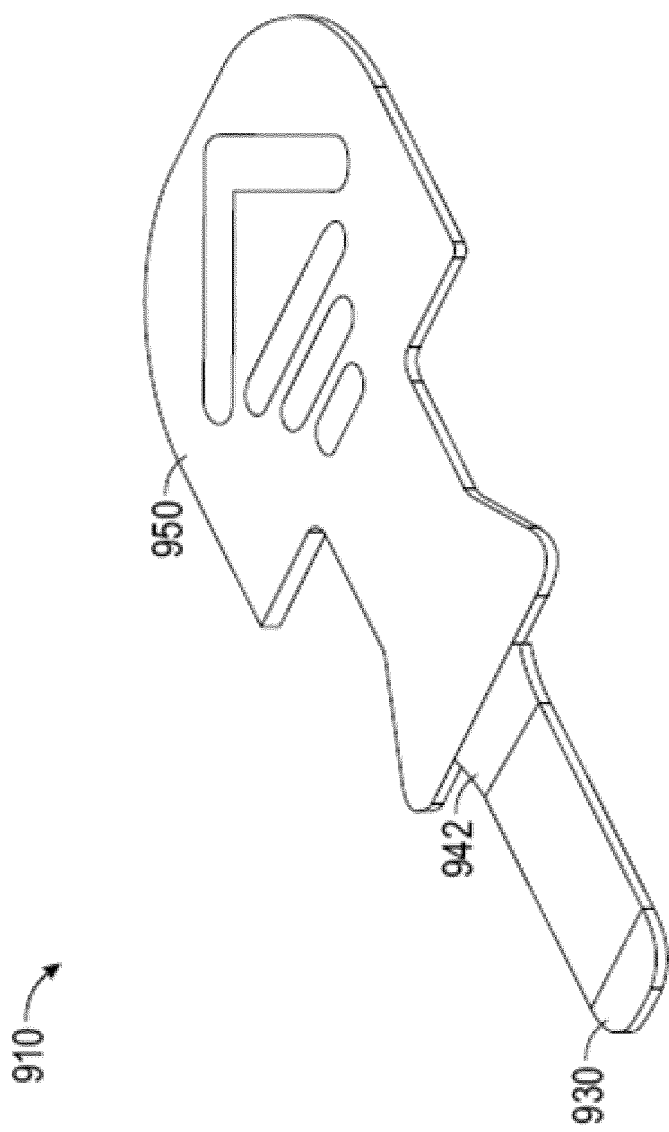

FIG. 9C illustrates a pull tab 910 according to some embodiments. Pull tab 910 can be used with any of the embodiments of the activation switch described herein, such as the switch 715. Pull tab 910 includes a region 930 that is configured to be in contact with the activation switch, such as the switch 715, when the pull tab is positioned on the PCB (see, for example, FIGS. 7 and 8A). The region 930 can include conductive material that is applied to the conductive paths of the activation switch to activate the switch when the pull tab 910 is pulled out. For instance, with reference to FIG. 7, the region 930 can be positioned in contact with the fingers of the switch 715. When the pull tab 910 is removed, conductive material is applied to the fingers causing the two sets of the fingers come in electrical contact with each other. This cases the isolation circuit to be in the "on" state.

As is illustrated in FIG. 9C, the pull tab 910 also includes a pattern 950 directing the user to pull to the left. In addition, the pull tab 910 includes a region 942 that can be coated with adhesive material in order to prevent inadvertent activation by keeping the pull tab 910 attached to the PCB before it is pulled by a user (see, for example, FIGS. 8A-8B).

In some embodiments, conductive material in the region 930 includes silver, which can be applied to or deposited in the region 930 as silver ink. When the pull tab is pulled by a user, silver ink from the region 930 can be applied across the activation switch to complete step 1 of the activation. For example, in case of the switch 715 illustrated in FIG. 7, application of the silver ink from the region 930 to the conductive fingers of the switch can create one or more short circuits across the fingers causing the switch 715 to turn on. In some implementations, a single or multiple layers of silver ink can be printed in the region 930.

In certain embodiments, in addition to or instead of silver, other conductive materials, formulations, or compounds can be deposited in the region 930. This can include carbon, gold, palladium, or the like. In some cases, it may be advantageous to use material, formulation, or compound that does not easily oxidise.

In certain embodiments, the pull tab 910 can be made of plastic. Conductive material in the region 930 can be applied to the plastic material by a suitable technique, such as screen printing, inject printing, sputtering, electro-depositing, plating, thin film bonding, or the like.

In some implementations, an activation switch can be turned off (instead of being turned on) during step 1 of activation. In such cases, pulling a pull tab can cause the activation switch to cease conducting. Although the foregoing describes a pull tab, additional or alternative force or forces can be applied to complete step 1 of the activation. Such forces can include pushing, pressing, or the like.

Figure 10:
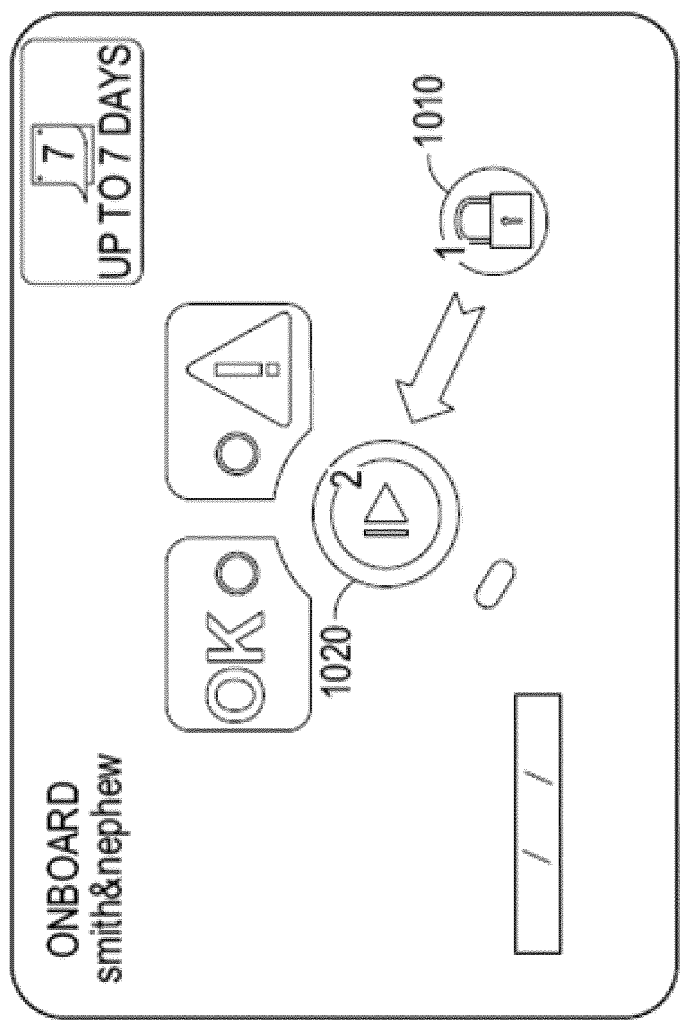
FIG. 10 illustrates a front view of a two-step activation PCB according to some embodiments.

FIG. 10 illustrates a front view of a two-step activation PCB according to some embodiments. Instead of a pull tab, a dome-type switch 1010 is used for step 1 activation, and another dome-type switch 1020 is used for step 2 activation. In some embodiments, step 1 activation with the first switch 1010 may be timed, such that the step 2 activation with switch 1020 may need to be pressed within certain time of activating switch 1010 of step 1. In some embodiments, either or both of the steps may require pressing and holding the dome-type switches 1010 and/or 1020 for an extended period of time for activations. In some embodiments, the two steps may be merged into one switch differentiating the activation steps based on duration of the press. For instance, a prolonged press of the switch may perform step 1 activation, followed by a short press to perform step 2 activation. As one skilled in the art will recognize, various types of switches with various operating mechanisms may be employed for the two-step activation.

Electronic Assembly Incorporated Within the Wound Dressing

Figure 11:
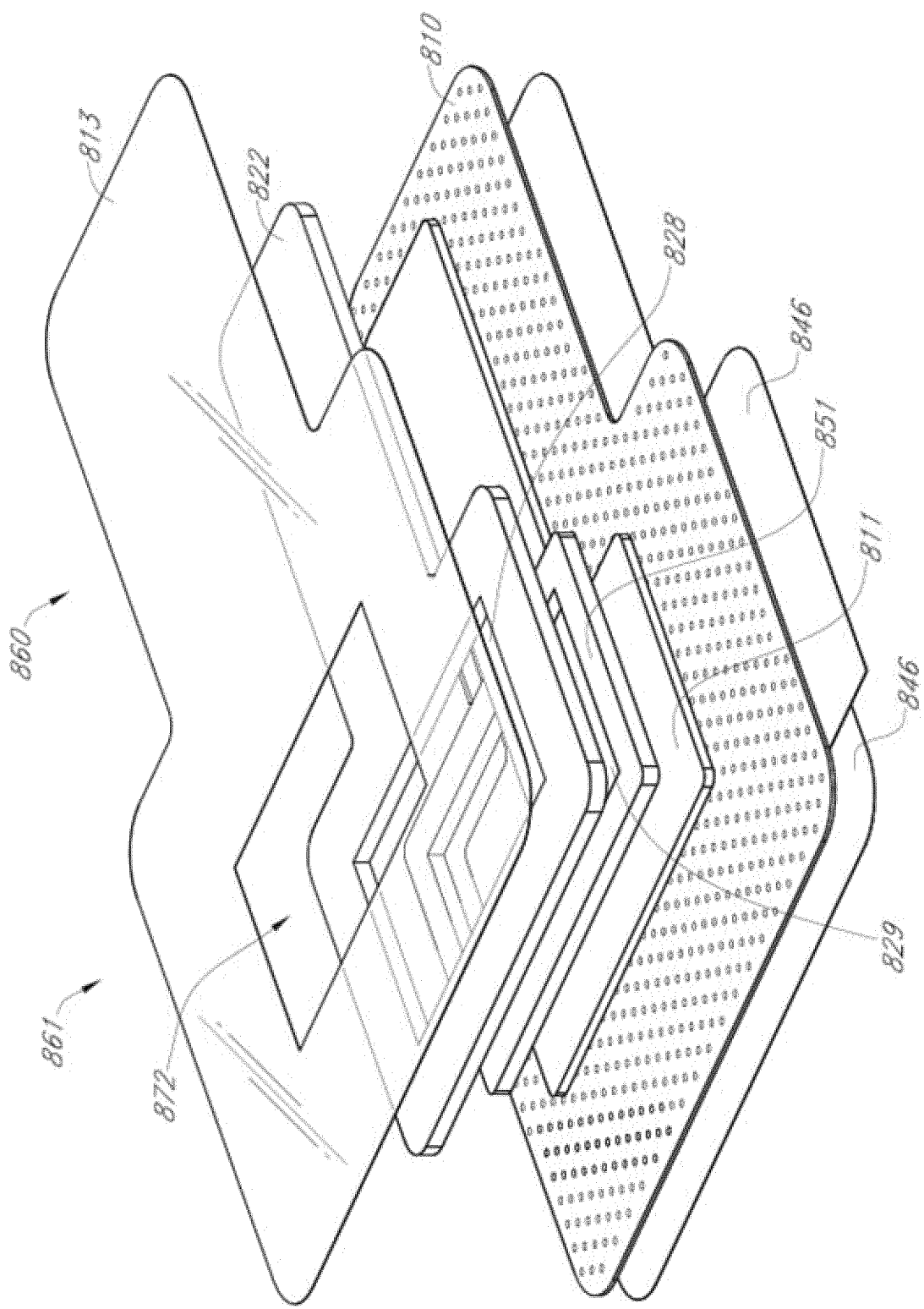
FIG. 11 illustrates wound dressing layers of a wound dressing for use with an electronics assembly according to some embodiments.

FIG. 11 illustrates wound dressing layers incorporating the electronics components within the wound dressing according to some embodiments. The dressing layers and components of FIG. 11 can be similar to the dressing layers and components described in FIGS. 1A-1C or in any other embodiments described herein. FIG. 11 illustrates a wound dressing with a wound contact layer 810 configured to contact the wound. The wound contact layer 810 can be a similar material and have a similar function as the wound contact layer described with reference to FIGS. 1A-1C. A transmission layer or spacer layer 811 is provided over the wound contact layer. The transmission layer or spacer layer 811 can be a similar material and have a similar function as the transmission layer or spacer layer described with reference to FIGS. 1A-1C. The transmission layer 811 can assist in transmitting and distributing negative pressure over the wound site.

A first layer of apertured absorbent material 851 can be provided over the transmission layer 811. The first apertured absorbent layer 851 can include one or more apertures 829. In some embodiments, the aperture 829 can be sized and shaped to fit an electronics assembly and/or electronics unit therein. The first apertured absorbent layer 851 can be sized and shaped to the size of the electronics area 861 and does not extend into the absorbent area 860. In some embodiments, the aperture 829 can be shaped and sized to fit the electronics assemblies as described herein.

A second apertured absorbent layer 822 can be provided over the first absorbent layer 851. In some embodiments, the second absorbent layer 822 includes one or more apertures 828. The second absorbent layer 822 can be sized and shaped to the size of the electronics area 861 and the absorbent area 860. In some embodiments, the aperture 828 can be shaped and sized to fit the electronics assemblies as described herein. The first and second absorbent layers 851 and 822 can be a similar material and have a similar function as the absorbent layer described with reference to FIGS. 1A-1C.

A cover layer or backing layer 813 can be positioned over the absorbent material 822. The cover layer or backing layer 813 can be a similar material and have a similar function as the cover layer or backing layer described with reference to FIGS. 1A-1C. The cover layer 813 can form a seal to the wound contact layer 810 at a perimeter region enclosing the absorbent layers 822 and 851 and the transmission layer 811. In some embodiments, the cover layer 813 can be a flexible sheet of material that forms and molds around the dressing components when they are applied to the wound. In other embodiments, the cover layer 813 can be a material that is preformed or premolded to fit around the dressing components as shown in FIG. 11. As used herein, the terms cover layer and backing layer can be used interchangeably to refer to the layer of material in the dressing configured to cover the layers of the wound dressing.

In some embodiments, the cover layer or backing layer 813 can include an aperture 872. The aperture 372 can be positioned over at least a portion of the aperture 828 in the absorbent layer 822 to allow access and fluid communication to at least a portion of the absorbent layers 822 and 851, transmission layer 811, and would contact layer 810 positioned below.

An electronics assembly can be positioned in the apertures 828, 829, and 872 of the first and second absorbent material 851 and 822 and the cover layer 813. The electronics assembly can include a pump, power source, and a printed circuit board as described herein.

Before use, the dressing can include one or more delivery layers 846 adhered to the bottom surface of the wound contact layer. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Figure 12A:
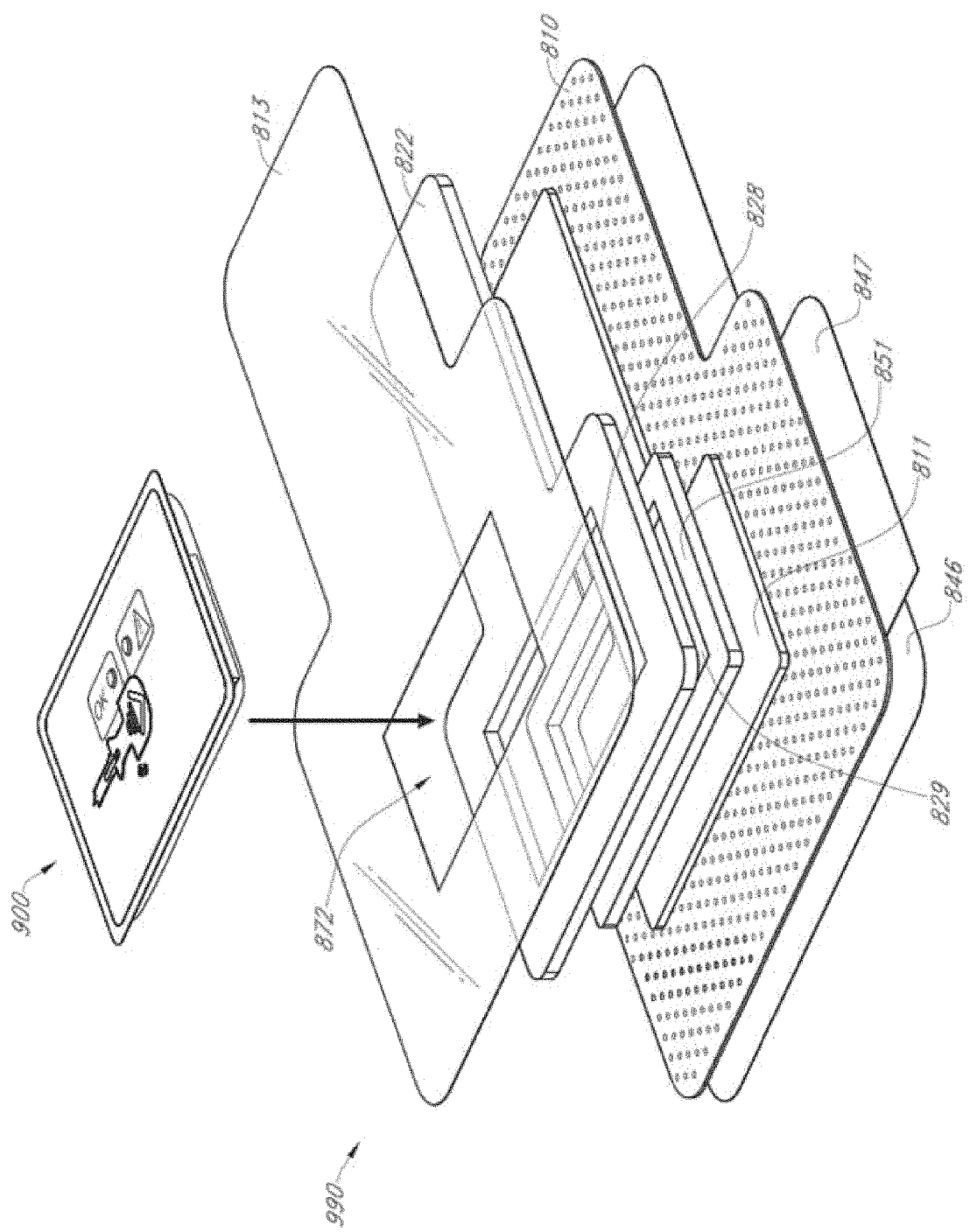
FIG. 12A illustrates a wound dressing incorporating an electronics assembly within the wound dressing layers according to some embodiments.

FIG. 12A illustrates a wound dressing incorporating an electronics assembly 900 within the wound dressing layers 990 according to some embodiments. The electronics assembly 900 can be provided within the aperture 872 in the cover layer and apertures 829 and 828 in the first and second absorbent layers. In some embodiments, the electronics assembly 900 can seal to the outer perimeter of the aperture 872 of the cover layer.

The electronics assembly 900 can include the pump inlet protection mechanism extending from and sealed to the film as described herein. The electronics assembly 900 can be positioned within the apertures 872, 829, 828 in the cover layer and absorbent layer(s) as shown in FIG. 12A. In some embodiments, the perimeter of the electronics assembly 900 can be sealed to a top surface of the outer perimeter of the aperture 872 in the cover layer as shown in FIG. 12A. In some embodiments, the electronics assembly 900 is sealed to the cover layer 813 with a sealant gasket, adhesive, heat welding, adhesive bonding, ultrasonic welding, RF welding, or any other attachment or bonding technique. In some embodiments, the electronics assembly 900 can be permanently sealed to the cover layer 813 and could not be removed from the cover layer without destroying the dressing.

In some embodiments, the electronics assembly 900 can be utilized in a single dressing and disposed of with the dressing. In other embodiments, the electronics assembly 900 can be utilized in a series of dressings.

Figure 12B:
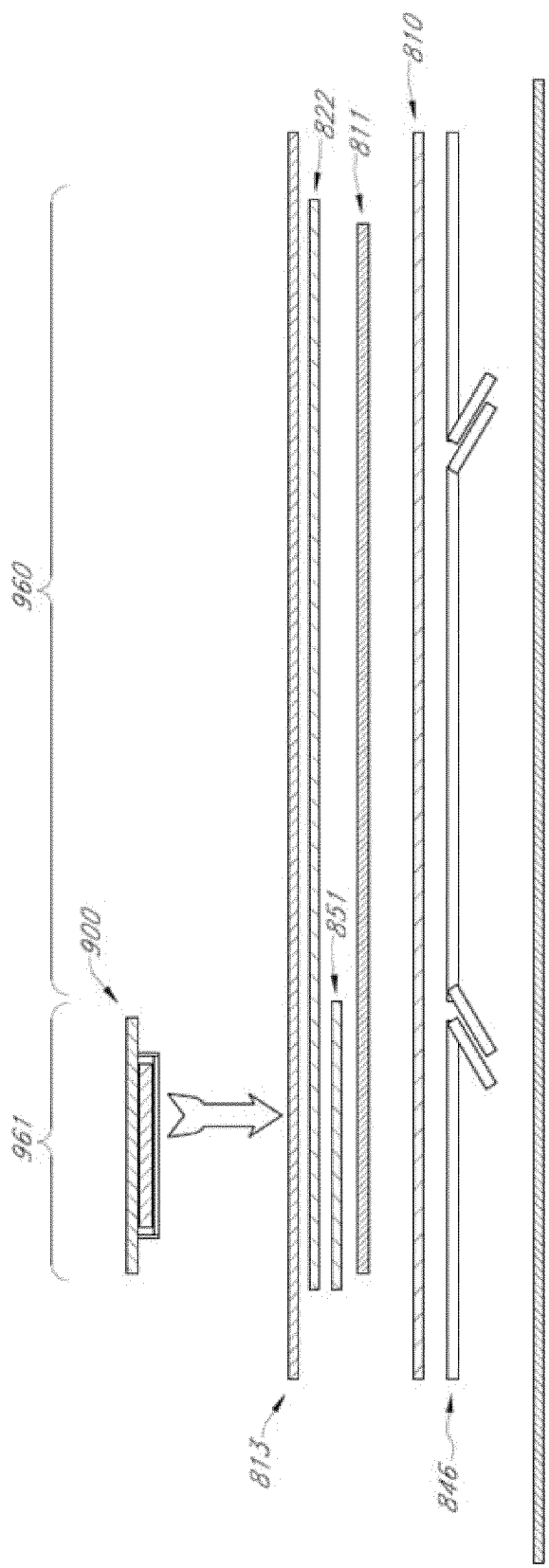
FIG. 12B illustrates a cross sectional layout of the material layers of the wound dressing incorporating an electronics assembly within the dressing according to some embodiments.

FIG. 12B illustrates a cross sectional layout of the material layers of the wound dressing incorporating an electronics assembly within the dressing according to some embodiments. The dressing included multiple material layers and an electronics assembly 900. The wound dressing can include an electronics area 961 including the electronics and an absorbent area or dressing area 960 that is intended to be applied to the wound as described with reference to FIGS. 1A-1C.

As described herein, the one or more material layers can extend into both the electronics area 961 and the dressing area 960. The dressing can include a wound contact layer 810, transmission layer 811, absorbent layers 822 and 851, and a cover or backing layer 813 as illustrated in FIG. 12B. The absorbent layers 822 and 851 and cover layer 813 can include recesses or cutouts to receive the components of the electronics assembly 900 as described with reference to FIG. 12A. In some embodiments, the small apertured absorbent layer 851 can be positioned on top of the large apertured absorbent layer 822. In other embodiments, as illustrated in FIGS. 9A-9B the small apertured absorbent layer 851 can be positioned below of the large apertured absorbent layer 922.

In some embodiments, the electronics assembly 900 can be inserted and affixed in the dressing layers. As illustrated in FIG. 12A, the lower wound facing face of the film enclosing the electronics assembly can be sealed directly to the upper surface of the cover layer 813 of the dressing.

Before use, the dressing can include a delivery layer 846 adhered to the bottom surface of the wound contact layer 810. The delivery layer 846 can cover adhesive or apertures on the bottom surface of the wound contact layer 810. In some embodiments, the delivery layer 846 can provided support for the dressing and can assist in sterile and appropriate placement of the dressing over the wound and skin of the patient. The delivery layer 846 can include handles that can be used by the user to separate the delivery layer 846 from the wound contact layer 810 before applying the dressing to a wound and skin of a patient.

Figure 13:
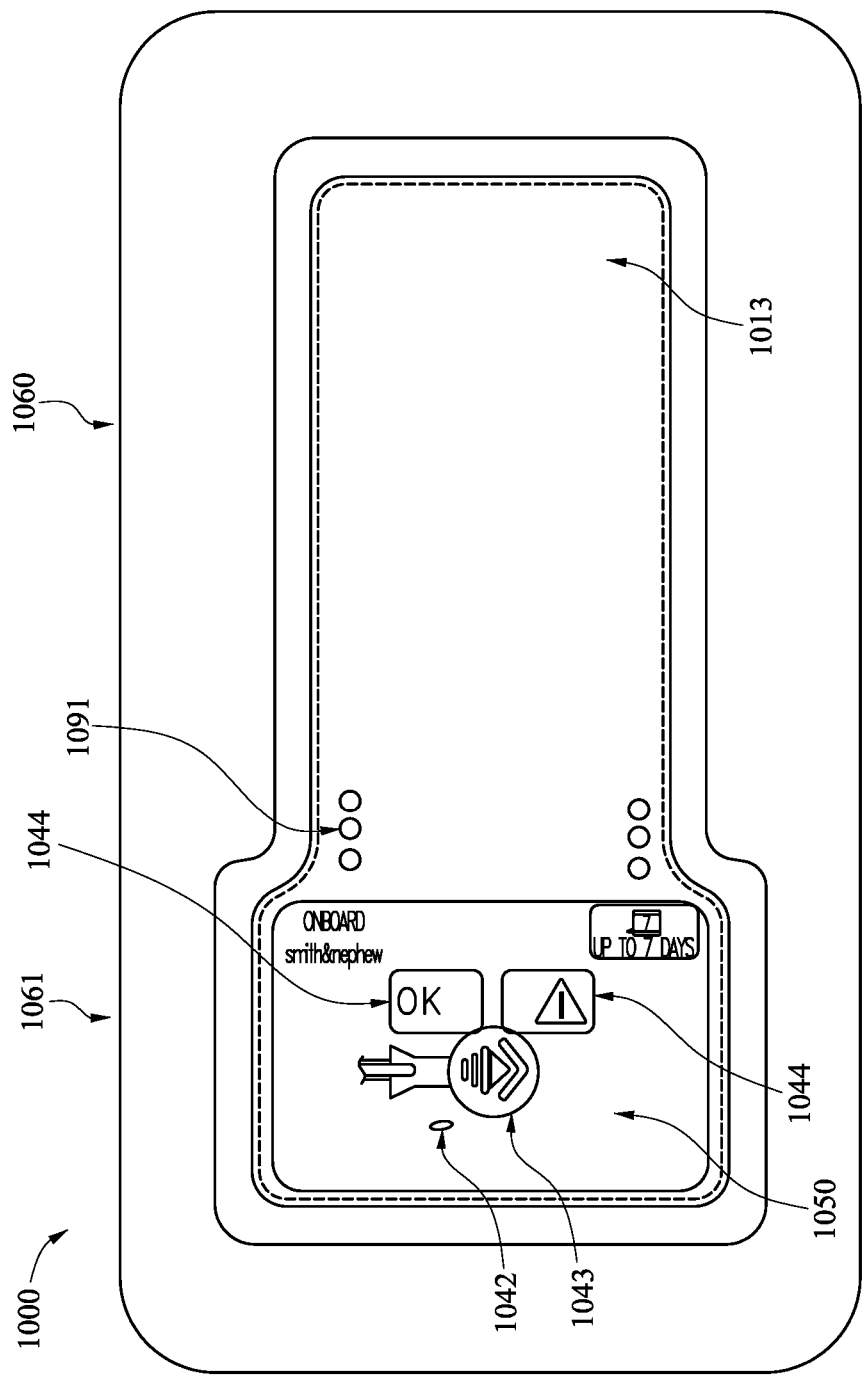
FIG. 13 illustrates a wound dressing incorporating an electronics assembly and negative pressure indicators within the dressing layers according to some embodiments.

FIG. 13 illustrates a wound dressing incorporating an electronics assembly within the dressing layers according to some embodiments. As illustrated in FIG. 13, the wound dressing comprises an absorbent area 1060 and an electronics area 1061. The electronics assembly 1050 can be incorporated into the electronics area 1061 of the dressing. The outer perimeter of the electronics assembly 1050 can be sealed to the perimeter of the aperture (not shown) in the cover layer 1013 as described in more detail with reference to FIGS. 12A-12B.

FIG. 13 illustrates negative pressure indicators 1091 within the wound dressing to indicate when the components within the wound dressing 1000 are under negative pressure. As illustrated in FIG. 13, the wound dressing includes an absorbent area 1060 adjacent to or offset from an electronics area 1061. In some embodiments, the absorbent area 1060 can include absorbent material to absorb and retain fluids and/or wound exudate from the wound. In some embodiments, the electronics area 1061 can include the electronics assembly and/or electronics components as described herein. The negative pressure indicator can be a mechanical indicator. In some embodiments, the negative pressure indicator can be an indicator that does not require direct line of sight from the patient. For example, the negative pressure indicator can be an indicator that can be touched or felt by a patient or user. The negative pressure indicator 1091 can be aperture(s) or cut out(s) in an absorbent material of the dressing. Once negative pressure is applied under the cover layer, the dressing will tighten and the cover layer will compress as it sucks down into the aperture(s) or cut out(s) in the absorbent material to indicate negative pressure is applied.

FIG. 13 illustrates a top view of an embodiment of the wound dressing incorporating an electronic assembly within the dressing. In some embodiments, the plate of the electronics assembly 1050 can include the features and text of an electronics label. In other embodiments, an electronics label can be secured or adhered to the plate of the electronics assembly 1050. In some embodiments, the plate and/or label can include one or more holes or apertures positioned over or in communication with the switch, visual indicators, and/or pump exhaust mechanism vent(s) on the flexible circuit board. In some embodiments, the plate and/or label can include transparent or semi-transparent visual indicator portions 1044 to allow the light from the visual indicators on the flexible circuit board to be visible. Additionally, as illustrated in FIG. 13, the transparent or semi-transparent visual indicator portions 1044 of the plate and/or label can include visual symbols or words to communicate a condition of the dressing or electronics. In some embodiments, the plate and/or label can include embossed features for a switch cover 1043. In some embodiments, the embossed features of the switch cover 1043 can prevent accidental activation or deactivation of the device as described herein. In some embodiments, the switch or switch cover 1043 can include a tab on the switch, which can be a pull tab described herein. In some embodiments, the plate and/or label can include apertures or holes 1042 in fluid communication with the vent in the pump exhaust mechanism to vent air exhausted from the pump.

In some embodiments, various shapes and sizes for the wound dressing can incorporate an electronics assembly. The wound dressing with embedded electronics assembly can be any shape or size to accommodate various types of wounds and conform to the shapes and contours of the patient's body. For example, the wound dressing with embedded electronics can have a rectangular, rounded rectangular, square, T shaped, or any other shape or design. The wound dressing can have a longitudinal length that is parallel to a longitudinal axis that extends the length of the dressing passing through the electronics area and absorbent area. The absorbent area can have a longitudinal axis extending parallel to the longitudinal axis of the dressing. In some embodiments, the dressing has a length that is longer parallel to the longitudinal axis than it is wide. The electronics assembly can have a longitudinal axis that is perpendicular to the longitudinal axis of the absorbent area. In some embodiments, electronics assembly can have a length parallel to its longitudinal axis that is longer than it is wide. In some embodiments, the absorbent area of the wound dressing can be an elongated rectangular shape that includes a length of the absorbent area that is greater than the width of the absorbent area. In some embodiments, the absorbent area of the wound dressing can have a square shape that includes a length of the absorbent area that is substantially equal to or equal to the width of the absorbent area. In some embodiments, the wound dressings with embedded electronics described herein can be rectangular or rounded rectangular shaped as illustrated with reference to FIGS. 1A-1C. In other embodiments, the wound dressings with embedded electronics described herein can be a T shaped as illustrated with reference to FIGS. 11 to 13.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract, and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A negative pressure wound therapy system comprising:
   a wound dressing configured to be placed over a wound of a patient;
   a source of negative pressure disposed on or within the dressing, the source of negative pressure configured to provide negative pressure to the wound; and
   an electronic circuit disposed on or within the dressing, the electronic circuit comprising:
      a controller configured to operate the source of negative pressure;
      a power source configured to supply power to the controller; and
      an isolation circuit in electrical communication with the power source and the controller, the isolation circuit configured to operate in a first state in which the isolation circuit prevents application of power to the source of negative pressure and in a second state in which the isolation circuit permits application of power to the source of negative pressure, the isolation circuit comprising an activation switch configured to be activated and to cause the isolation circuit to operate in the second state;
      wherein the activation switch is activated by a tab configured to be removed by a user; and
      wherein in the first state, the tab is configured to complete an electrical path in the isolation circuit and prevent activation of the activation switch.

2. The system of claim 1, wherein the activation switch is configured to remain activated following removal of the tab.

3. The system of claim 1, wherein the tab comprises conductive material configured to complete an electrical path in the isolation circuit and prevent activation of the activation switch.

4. The system of claim 3, wherein the conductive material comprises silver ink deposited in a region of the tab, wherein the region is configured to make electrical contact with the isolation circuit.

5. The system of claim 1, wherein the electronic circuit further comprises a boost converter configured to increase power supplied by the power source and to provide increased power to the source of negative pressure.

6. The system of claim 5, further comprising at least one energy storing component configured to store energy supplied by the boost converter and to power the source of negative pressure with the stored energy.

7. The system of claim 1, wherein the electronic circuit further comprises an operation switch configured to activate and pause provision of negative pressure by the source of negative pressure.

8. The system of claim 7, wherein the electronic circuit is configured to not activate the provision of negative pressure by the source of negative pressure when the isolation circuit is in the first state and the operation switch is activated.

9. The system of claim 1, wherein the isolation circuit comprises a latching circuit.

10. The system of claim 9, wherein the latching circuit is configured to cause the isolation circuit to remain in the second state in response to removal of the tab.

11. The system of claim 10, wherein the latching circuit is configured to cause the isolation circuit to remain in the second state in response to deactivation of the activation switch subsequent to removal of the tab.

12. The system of claim 1, wherein the power source is nonremovable.

13. The system of claim 1, further comprising an indicator configured to provide at least one of an indication that the activation switch has not been activated or an indication that the activation switch has been activated.

14. The system of claim 1, wherein the controller is configured to be powered by the power source when the isolation circuit is in the first or second state.

15. A method of operating a negative pressure wound therapy apparatus comprising a wound dressing, a source of negative pressure disposed on or within the wound dressing, and an electronic circuit disposed on or within the wound dressing and configured to operate the source of negative pressure, the method comprising:
   activating an activation switch responsive to removal of a tab configured to complete an electrical path in the electronic circuit and prevent activation of the activation switch, the activation switch configured to cause the electronic circuit to transition from operating in a first state in which power is not applied to the source of negative pressure to operating in a second state in which power is applied to the source of negative pressure; and
   activating the source of negative pressure to provide negative pressure to the wound dressing.

16. The method of claim 15, wherein the apparatus has been sterilized with Ethylene oxide (EtO) while the electronic circuit was operating in the first state in which no power was applied to the source of negative pressure.

17. A method of operating a negative pressure wound therapy apparatus comprising a wound dressing, a source of negative pressure disposed on or within the wound dressing, and an electronic circuit disposed on or within the wound dressing and configured to operate the source of negative pressure, the method comprising:
   maintaining an isolation circuit of the electronic circuit in an inactive state during which no power is supplied to the source of negative pressure;
   in response to activation of an activation switch of the electronic circuit, transitioning the isolation circuit to an active state during which power is supplied to the source of negative pressure, wherein activating the activation switch comprises removing a tab that completes an electrical path in the isolation circuit and prevents activation of the activation switch when the isolation circuit is in the inactive state; and
   activating the source of negative pressure when the isolation circuit is in the active state.

18. The method of claim 17, wherein the apparatus is sterilized when the isolation circuit is in the inactive state.

* * * * *